United States Patent
Kirchhoff et al.

(10) Patent No.: US 11,634,517 B2
(45) Date of Patent: Apr. 25, 2023

(54) PYRROLE-BASED POLYMERS FOR METAL EXTRACTION, ANALYSIS, AND REMOVAL

(71) Applicant: The University of Toledo, Toledo, OH (US)

(72) Inventors: Jon R. Kirchhoff, Toledo, OH (US); Ahmad Rohanifar, Toledo, OH (US); Govind Sharma Shyam Sunder, Toledo, OH (US)

(73) Assignee: The University of Toledo, Toledo, OH (US)

( * ) Notice: Subject to any disclaimer, the term of this patent is extended or adjusted under 35 U.S.C. 154(b) by 747 days.

(21) Appl. No.: 16/583,751

(22) Filed: Sep. 26, 2019

(65) Prior Publication Data

US 2020/0102410 A1 Apr. 2, 2020

Related U.S. Application Data

(60) Provisional application No. 62/737,199, filed on Sep. 27, 2018.

(51) Int. Cl.
| | |
|---|---|
| *C08F 26/06* | (2006.01) |
| *C02F 1/26* | (2023.01) |
| *C02F 1/28* | (2023.01) |
| *C22B 3/42* | (2006.01) |
| *G01N 33/18* | (2006.01) |
| *G01N 33/20* | (2019.01) |
| *B01J 20/26* | (2006.01) |
| *C02F 1/68* | (2023.01) |
| *C02F 101/20* | (2006.01) |

(52) U.S. Cl.
CPC ............ *C08F 26/06* (2013.01); *C02F 1/26* (2013.01); *C02F 1/285* (2013.01); *C22B 3/42* (2013.01); *G01N 33/1813* (2013.01); *G01N 33/20* (2013.01); *B01J 20/26* (2013.01); *C02F 1/683* (2013.01); *C02F 2101/20* (2013.01)

(58) Field of Classification Search
None
See application file for complete search history.

(56) References Cited

PUBLICATIONS

O'Riordan et al. (Anal. Chem. 1986, 58, 128-131). (Year: 1986).*

* cited by examiner

*Primary Examiner* — Clare M Perrin
(74) *Attorney, Agent, or Firm* — MacMillan, Sobanski & Todd, LLC

(57) ABSTRACT

Materials and methods for extracting metals from solutions, involving a polymer of Formula A are described:

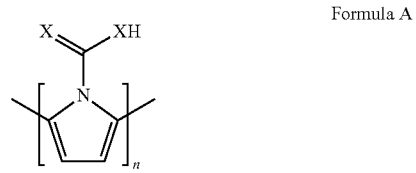

Formula A where each X is independently either S or O, and n is an integer greater than 1.

17 Claims, 33 Drawing Sheets
(26 of 33 Drawing Sheet(s) Filed in Color)

PYRROLE-BASED POLYMERS FOR METAL EXTRACTION, ANALYSIS, AND REMOVAL

RELATED APPLICATIONS

This application claims priority to U.S. Provisional Application No. 62/737,199, filed under 35 U.S.C. § 111(b) on Sep. 27, 2018, the entire disclosure of which is incorporated herein by reference for all purposes.

STATEMENT REGARDING FEDERALLY SPONSORED RESEARCH

This invention was made with no government support. The government has no rights in this invention.

BACKGROUND

Heavy metal contamination in water is a global concern due to their toxicity and carcinogenicity, and thus their detection and removal is of great importance to ensure the quality of the water resources. Some heavy metals such as cobalt, copper, and zinc are essential for the human body in low levels, but can be very harmful in elevated levels. Other heavy metals including cadmium, nickel, and lead are highly toxic even in low levels. According to the World Health Organization (WHO), the maximum limits for Cd, Ni, and Pb are 3, 20, and 10 µg $L^{-1}$, respectively. Cadmium is very toxic even at low concentrations and can cause lung cancer, renal failure, gastrointestinal diseases, birth defects, and anemia. Nickel is another toxic heavy metal which enters wastewater from industrial sources. Nickel can cause breathing problems, diarrhea, and neurological problems. Battery manufacturing, galvanization, smelting, mining, printing, and alloy industries are among the main source of nickel utilization.

Heavy metals enter the environment from many industrial and natural sources, and may be hazardous. For example, lead is a neurotoxin which has reportedly given rise to harmful effects in the body such as reduction of enzymatic activity, kidney dysfunction, and neuromuscular difficulties. A prime example is the Flint water crisis, which began in 2014 when corrosive Flint River water that was not treated properly caused lead from aging pipes to leach into the water supply. This resulted in extremely elevated lead levels, exposing about 100,000 residents to high levels of lead in the drinking water. This example shows the importance of developing precise and accurate methods for the early detection of trace amounts of heavy metals in water samples, as well as for removal of heavy metals from water.

Several sorbent materials have been used in solid-phase extraction-based methods for extraction, removal, and determination of heavy metals. Many of these sorbents such as zeolites, natural clays, and activated carbons use a physical adsorption mechanism based on trapping of the analyte with weak van der Waals forces into the pores of the adsorbent. This mechanism is usually not very selective and various types of interferences including from organic molecules, which can adsorb with the same mechanism to these kinds of sorbents and compete with target metal ions, adsorbing and desorbing along with the analyte. Furthermore, metals exist at low concentration levels and may form complexes in the matrix which cause interferences with detection and quantification methods.

Detection and quantification of heavy metals is necessary in order to produce safe drinking water. Robust and sensitive techniques are needed to detect trace heavy metals in water. Currently, several analytical microextraction and preconcentration techniques are used to determine heavy metals. These include liquid-liquid extraction (LLE), dispersive liquid-liquid microextraction (DLLME), liquid phase microextraction (LPME), and solid phase extraction (SPE). However, known methods are not very efficient, and may have a slow adsorption equilibrium.

There is a need in the art for new and improved materials and methods for detecting, quantifying, or extracting heavy metals in solutions.

SUMMARY

Provided is a composition comprising Formula A:

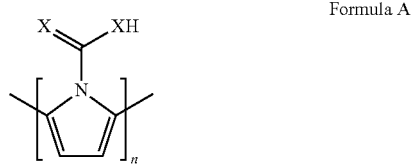

Formula A wherein each X is independently either S or O, and n is an integer greater than 1. Also provided are salts, stereoisomers, racemates, hydrates, solvates, polymorphs, and complexes of Formula A. In certain embodiments, n ranges from 2 to about 10,000. In certain embodiments, n ranges from about 50 to about 5,000. In certain embodiments, n ranges from about 100 to about 2,000. In certain embodiments, n ranges from about 150 to about 1865. In certain embodiments, n is about 300.

Further provided is a composition comprising Formula I:

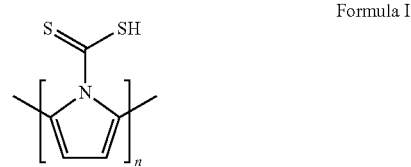

Formula I wherein n is an integer greater than 1. Also provided are salts, stereoisomers, racemates, hydrates, solvates, polymorphs, and complexes of Formula I. In certain embodiments, n ranges from 2 to about 10,000. In certain embodiments, n ranges from about 50 to about 5,000. In certain embodiments, n ranges from about 100 to about 2,000. In certain embodiments, n ranges from about 150 to about 1865. In certain embodiments, n is about 300. In certain embodiments, the composition is dispersed in an aqueous solution. In certain embodiments, the composition is within pores of a filter. In certain embodiments, the composition is chelated to a metal. In particular embodiments, the metal is selected from the group consisting of Co, Ni, Cu, Zn, Cd, and Pb.

Further provided is a composition comprising Formula II:

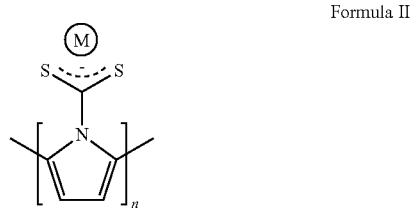

Formula II where n is an integer greater than 1; and wherein M is a metal cation comprising a metal selected from the group consisting of Co, Ni, Cu, Zn, Cd, and Pb. Also provided are salts, stereoisomers, racemates, hydrates, solvates, and polymorphs of Formula II. In certain embodiments, n ranges from 2 to about 10,000. In certain embodiments, n ranges from about 50 to about 5,000. In certain embodiments, n ranges from about 100 to about 2,000. In certain embodiments, n ranges from about 150 to about 1865. In certain embodiments, n is about 300.

Further provided is a composition comprising Formula IV:

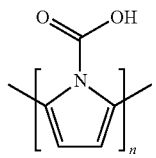

Formula IV wherein n is an integer greater than 1. Also provided are salts, stereoisomers, racemates, hydrates, solvates, polymorphs, and complexes of Formula IV. In certain embodiments, n ranges from 2 to about 10,000. In certain embodiments, n ranges from about 50 to about 5,000. In certain embodiments, n ranges from about 100 to about 2,000. In certain embodiments, n ranges from about 150 to about 1865. In certain embodiments, n is about 300. In certain embodiments, the composition is dispersed in an aqueous solution. In certain embodiments, the composition is within pores of a filter. In certain embodiments, the composition is chelated to a metal. In particular embodiments, the metal is selected from the group consisting of Be, Mg, V, Cr, Mn, Fe, Co, Ni, Cu, Zn, Ga, As, Se, Rb, Ag, Cd, Cs, Ba, Au, Tl, Th, Pb, and U, or a rare earth element (REE) selected from the group consisting of La, Ce, Pr, Nd, Sm, Eu, Gd, Dy, Ho, Er, Tm, Yb, and Lu.

Further provided is a composition comprising Formula V:

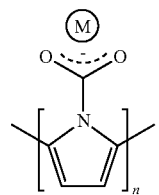

Formula V where n is an integer greater than 1; and wherein M is a metal cation comprising a metal selected from the group consisting of Be, Mg, V, Cr, Mn, Fe, Co, Ni, Cu, Zn, Ga, As, Se, Rb, Ag, Cd, Cs, Ba, Au, Tl, Th, Pb, and U, or a rare earth element selected from the group consisting of La, Ce, Pr, Nd, Sm, Eu, Gd, Dy, Ho, Er, Tm, Yb, and Lu. Also provided are salts, stereoisomers, racemates, hydrates, solvates, and polymorphs of Formula V. In certain embodiments, n ranges from 2 to about 10,000. In certain embodiments, n ranges from about 50 to about 5,000. In certain embodiments, n ranges from about 100 to about 2,000. In certain embodiments, n ranges from about 150 to about 1865. In certain embodiments, n is about 300.

Further provided is a method for removing a metal from a solution, the method comprising contacting a solution containing at least one metal ion with a polymer in order to chelate the metal ion to the polymer and thereby form a chelation complex, and removing the chelation complex from the solution so as to remove the metal from the solution, wherein the polymer comprises Formula A:

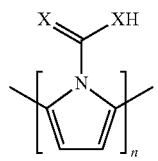

Formula A wherein each X is independently either S or O, and n is an integer greater than 1.

In certain embodiments, the polymer comprises poly(1H-pyrrole-1-carbodithioic acid) (PPy-$CS_2$), poly(1H-pyrrole-1-carboxylic acid) (PPy-$CO_2$), or a combination thereof. In certain embodiments, the metal comprises Be, Mg, V, Cr, Mn, Fe, Co, Ni, Cu, Zn, Ga, As, Se, Rb, Ag, Cd, Cs, Ba, Au, Tl, Th, Pb, U, or a rare earth element comprising La, Ce, Pr, Nd, Sm, Eu, Gd, Dy, Ho, Er, Tm, Yb, or Lu, or a combination thereof. In certain embodiments, the solution comprises water from a natural water source or drinking water. In certain embodiments, the removing comprises passing the solution through a filter to remove the polymer from the solution. In particular embodiments, the filter comprises pores having a size of about 0.2 microns.

Further provided is a method for detecting or quantifying metal ions, the method comprising dispersing a polymer into a solution containing metal ions at a first concentration in order to chelate the metal ions to the polymer, desorbing the metal from the polymer in order to produce a pre-concentrated solution containing the metal at a second concentration, wherein the second concentration is greater than the first concentration, and analyzing the pre-concentrated solution to detect or quantify the metal, wherein the polymer comprises Formula A:

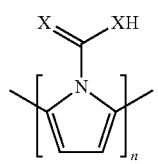

Formula A wherein each X is independently either S or O, and n is an integer greater than 1.

In certain embodiments, the dispersing of the composition comprises ultra-sonification.

In certain embodiments, the method further comprises a filtration, or other suitable separation, step before the desorbing step, to produce a purified solution with the metal removed.

In certain embodiments, the desorbing is conducted with an acid. In certain embodiments, the desorption is conducted with nitric acid ($HNO_3$), or methanol and DCM for desorption of organics. In particular embodiments, the nitric acid comprises 2 M $HNO_3$.

In certain embodiments, the solution contains multiple metals. In certain embodiments, the metal comprises Be, Mg, V, Cr, Mn, Fe, Co, Ni, Cu, Zn, Ga, As, Se, Rb, Ag, Cd, Cs, Ba, Au, Tl, Th, Pb, U, or a rare earth element comprising La, Ce, Pr, Nd, Sm, Eu, Gd, Dy, Ho, Er, Tm, Yb, or Lu, or a combination thereof.

In certain embodiments, the solution comprises water from a natural water source or drinking water.

In certain embodiments, the polymer is in the form of sorbent particles.

Further provided is a method for producing a sorbent material, the method comprising oxidizing 1H-pyrrole-1-carbodithioic acid (Py-CS$_2$) to produce poly(1H-pyrrole-1-carbodithioic acid). In certain embodiments, the oxidizing comprises reacting 1H-pyrrole-1-carbodithioic acid with FeCl$_3$. In certain embodiments, the oxidizing comprises reacting 1H-pyrrole-1-carbodithioic acid with ammonium persulfate.

Further provided is a method for producing a sorbent material, the method comprising N-functionalizing pyrrole with carboxylic acid to produce 1H-pyrrole-1-carboxylic acid (Py-CO$_2$), and polymerizing the 1H-pyrrole-1-carboxylic acid to produce poly(1H-pyrrole-1-carboxylic acid). In certain embodiments, the N-functionalizing comprises reacting pyrrole with CO$_2$ in the presence of a base. In particular embodiments, the base comprises potassium tert-butoxide. In certain embodiments, the polymerization comprises oxidizing the 1H-pyrrole-1-carboxylic acid with an oxidizing agent. In particular embodiments, the oxidizing agent comprises ammonium persulfate (APS).

Further provided is a sorbent material comprising a composition comprising Formula A:

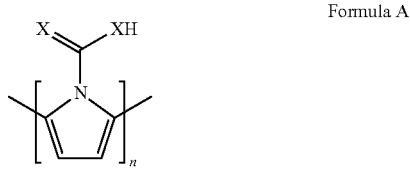

Formula A wherein each X is independently S or O, and n is an integer greater than 1, and the sorbent material further comprises a substrate. The composition may be deposited or coated on the substrate. In particular embodiments, the substrate comprises a conductive or magnetic material, silica, or a fiber. In certain embodiments, the composition is dispersed in an aqueous solution. In certain embodiments, the composition is within pores of a filter.

Further provided is a solid phase microextraction (SPME) fiber comprising a composition comprising Formula A:

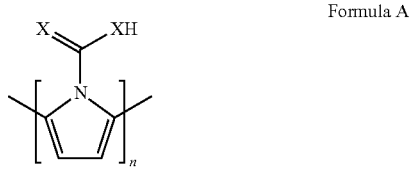

Formula A wherein each X is independently S or O, and n is an integer greater than 1, and the SPME fiber further comprises a fiber, wherein the composition is coated on the fiber.

Further provided is a kit for heavy metal testing, the kit comprising a first container housing a composition comprising Formula A:

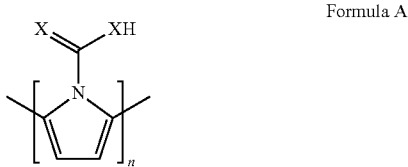

Formula A wherein each X is independently S or O, n is an integer greater than 1, and a second container housing one or more of an acid, a syringe, or a filter.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

DETAILED DESCRIPTION

Figure 1:
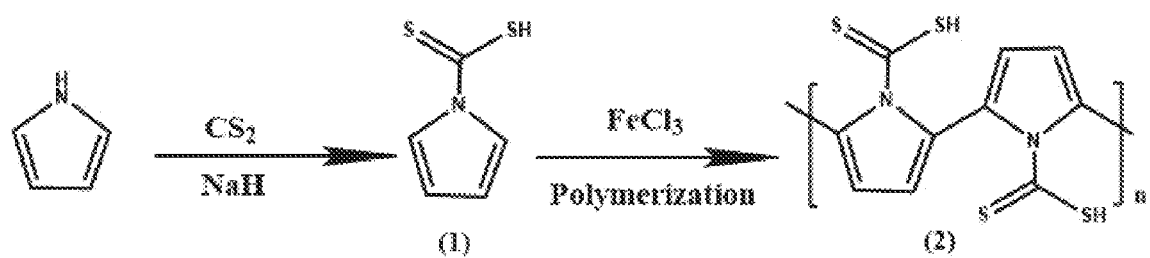
FIG. 1: Scheme 1, depicting the synthesis of poly(1H-pyrrole-1-carbodithioic acid) (PPy-CS$_2$).

Throughout this disclosure, various publications, patents, and published patent specifications are referenced by an identifying citation. The disclosures of these publications, patents, and published patent specifications are hereby incorporated by reference into the present disclosure in their entirety to more fully describe the state of the art to which this invention pertains.

In accordance with the present disclosure, polymeric materials may be used for efficient extraction and removal of heavy metals from solution. Provided herein are materials and methods for the detection of heavy metals in which the primary mechanism is chelation, not adsorption, which may minimize interferences.

Provided herein are pyrrole-based chelation polymers capable of extracting metals. The polymers may be produced by, for instance, the chemical oxidation of the pyrrole monomer, 1H-pyrrole-1-carbodithioic acid, to yield a dark solid polymer powder with fine particle sizes, or the N-functionalization of pyrrole with CO₂ and subsequent polymerization to produce poly(1H-pyrrole-1-carboxylic acid). Polymeric sorbents have been considered as alternatives to traditional sorbents because of their high surface area, mechanical strength, and possible regeneration. Polyaniline (PANI), polythiophene (PTh), and polypyrrole (PPy), as well as their nanocomposite derivatives, have been used for adsorbing different heavy metals. In polypyrrole, the nitrogen atom is considered to be responsible for heavy metal adsorption. However, the structure of polypyrrole clearly shows that the N atom is blocked by the attached hydrogen. In fact, the extraction ability of polypyrrole has been demonstrated to be less than the polymers described herein, under the same experimental conditions for synthesis of the polymers, extraction of metal ions, and desorption of the ions from the polymers.

The polymers described herein have the structural formula of Formula A:

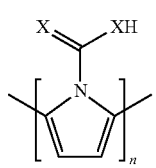

Formula A where each X is independently either S or O, and n is an integer greater than 1, such as an integer ranging from 2 to about 10,000. In certain embodiments, n ranges from 2 to about 10,000. In certain embodiments, n ranges from about 50 to about 5,000. In certain embodiments, n ranges from about 100 to about 2,000. In certain embodiments, n ranges from about 150 to about 1865. In certain embodiments, n is about 300. Also provided are salts, stereoisomers, racemates, hydrates, solvates, polymorphs, and complexes of Formula A.

One non-limiting example polymer of Formula A is known as poly(1H-pyrrole-1-carbodithioic acid), having the structural formula of Formula I:

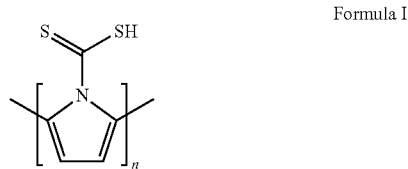

Formula I where n is an integer greater than 1, such as an integer ranging from 2 to about 10,000. In certain embodiments, n ranges from 2 to about 10,000. In certain embodiments, n ranges from about 50 to about 5,000. In certain embodiments, n ranges from about 100 to about 2,000. In certain embodiments, n ranges from about 150 to about 1865. In certain embodiments, n is about 300. Also provided are salts, stereoisomers, racemates, hydrates, solvates, polymorphs, and complexes of Formula I.

The polymer of Formula I may also be referred to as PPy-CS₂. PPy-CS₂ is easily handled in solid form. Advantageously, the monomer of Formula I is electropolymerizable on conductive surfaces of different geometries to yield Formula I. Thus, the polymer of Formula I may be formed on a wide variety of surfaces and substrates. However, the polymer is a free-standing material that can be produced as a powder, which is easily packed into a column or otherwise applied to a desired surface or apparatus. The polymer can also be formed on a variety of substrates such as silica particles. PPy-CS₂ may be produced according to Scheme 1, depicted in FIG. 1, in which PPy-CS₂ is labeled compound (2).

As described in the examples herein, PPy-CS₂ has been used to extract heavy metal ions by dispersion of the polymer by ultrasound in an aqueous solution of 6 metal ions at concentrations of 250 μg/L each (Co, Ni, Cu, Zn, Cd, and Pb). This technique is referred to as ultrasound assisted dispersive micro solid phase extraction. Removal of the metal ions from solution and recovery of the ions from the polymer occurred with greater than 94% efficiency as determined by ICP-MS. The sorbent polymer may also be utilized in solid-phase extraction (SPE) methods for extraction of larger amounts of metal ions. SPE applications are particularly relevant to new sorbent coatings that are important for quantitative extraction and trace analysis in complex matrices, especially for hazardous heavy metals.

PPy-CS₂ is polypyrrole (PPy) functionalized with CS₂. PPy is a conductive polymeric adsorbent that has been used for extraction of several organic and inorganic analytes. PPy is a cost-effective and porous material with excellent chemical and thermal stability, and with no reported solubility in water. These features make PPy a candidate for extraction of metal ions in aqueous solutions. Several studies have been performed for extraction of heavy metals using PPy, and PPy based composites with $Fe_3O_4$, carbon nanotubes (CNT), tenorite, and sawdust. In PPy and its composites, weak van der Waals forces are also responsible for the adsorption mechanism of heavy metals. Nitrogen atoms also can coordinate metal ions and enhance the extraction efficiency of the polymer. However, the N atoms in PPy are clearly blocked by the hydrogen atoms in PPy. As demonstrated in the examples herein, PPy-$CS_2$ is significantly better at extracting heavy metals than PPy. Without wishing to be bound by theory, it is believed that the sulfurs are advantageous for chelating metals. Methods of using PPy-$CS_2$ to extract heavy metals may also involve a very fast equilibrium time such as less than 5 minutes.

Figure 2:
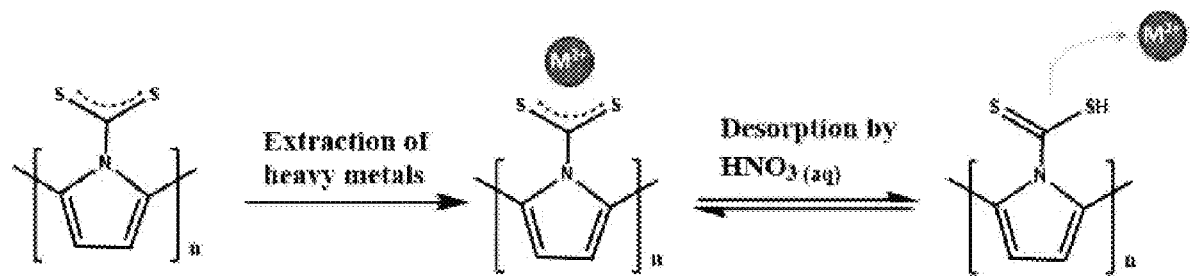
FIG. 2: Scheme 2, depicting the extraction and desorption of heavy metal ions using poly(1H-pyrrole-1-carbodithioic acid).

In accordance with the present disclosure, pyrrole may be derivatized with carbodithioic acid and polymerized to create a polymer with improved complexing ability. The $CS_2$ functional group with the two sulfur atoms acts as a bidentate chelating moiety (Scheme 2, FIG. 2). The functionalized pyrrole may be polymerized with an oxidizing agent such as, but not limited to, $FeCl_3$ or ammonium persulfate, in a suitable solvent such as methanol. Any of many suitable oxidants may be used to produce the polymer. The resulting polymer is more effective than previously reported polymers for metal extraction since the extraction mechanism is primarily chelation. Furthermore, sulfur is a soft electron donor atom with better affinity toward divalent transition metals, which are relatively soft cations. An additional important characteristic of carbodithioic acid is the dual functionality for deprotonation and protonation that allows for facile extraction and desorption of the metal ions. Carbodithioic acid can be deprotonated at neutral pH, and the electrostatic attraction between the negatively charged carbodithioate anion and the positively charge metal cations affords better chelation and therefore, more efficient extraction. However, in acidic conditions, the carbodithioate group can be protonated or neutral which helps the metal ions to release (desorption) for ease of analysis and reuse of the polymer. In effect, the PPy-$CS_2$ polymer is reversible and reusable, very stable, and provides fast extraction and recovery of the metal ions. Therefore, as described in the examples herein, this adsorbent polymer has been utilized in an analytical technique based on ultrasound assisted dispersive micro solid-phase extraction (UAD μ-SPE) for trace determination of heavy metals. The UAD μ-SPE technique allows the sorbent to interact quickly and uniformly with the metal ions, which may lead to an enhanced precision and reduced extraction time. The small particle size of the synthesized polymeric sorbent results in efficient dispersion in the sample solution for extraction and ease of collection during the sample filtration. Though UAD μ-SPE is discussed for exemplary purposes, UAD μ-SPE is by no means the only analytical method possible.

As noted, a method of extracting metals with PPy-$CS_2$ may involve chelation instead of adsorption. The PPy-$CS_2$ may form a chelation complex with a metal ion as shown in Formula II:

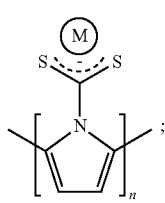

Formula II where M is a metal cation comprising a metal selected from the group consisting of Co, Ni, Cu, Zn, Cd, and Pb, and n is an integer greater than 1. For example, the poly(1H-pyrrole-1-carbodithioic acid) may form the following chelation product in solution with Pb:

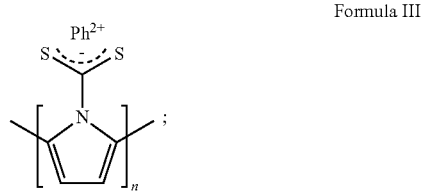

Formula III where n is an integer greater than 1.

The PPy-$CS_2$ polymeric material may quantitatively extract metal ions in a method that is sensitive, efficient, environmentally friendly, and cost effective for simultaneous extraction of heavy metals in natural water. PPy-$CS_2$ may thus be used in a variety of manners to extract or remove, and/or detect or quantify, metals in solutions.

Another non-limiting example polymer of Formula A is known as poly(1H-pyrrole-1-carboxylic acid) (PPy-$CO_2$), having the structural formula of Formula IV:

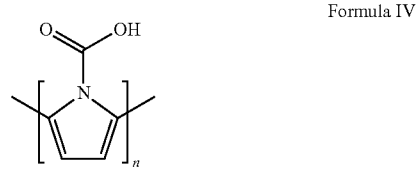

Formula IV where n is an integer greater than 1, such as an integer ranging from 2 to about 10,000. In certain embodiments, n ranges from 2 to about 10,000. In certain embodiments, n ranges from about 50 to about 5,000. In certain embodiments, n ranges from about 100 to about 2,000. In certain embodiments, n ranges from about 150 to about 1865. In certain embodiments, n is about 300. Also provided are salts, stereoisomers, racemates, hydrates, solvates, polymorphs, and complexes of Formula IV.

Figure 12:
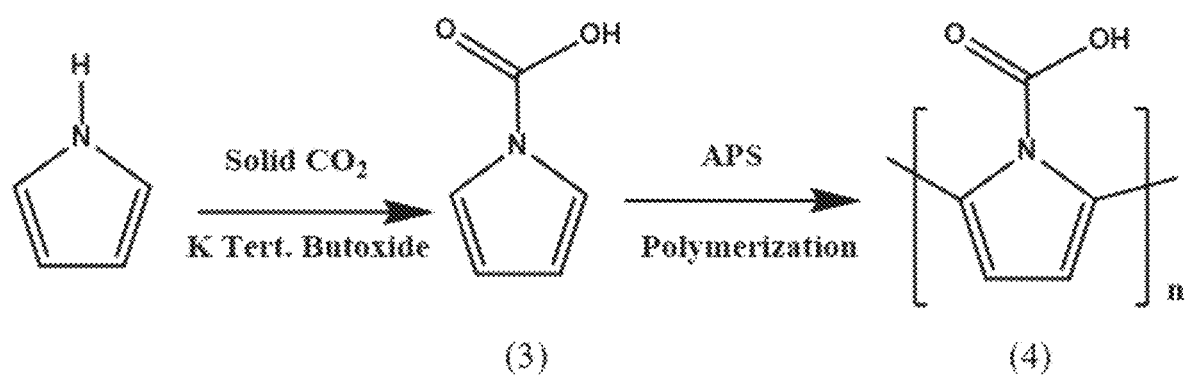
FIG. 12: Scheme 3, depicting the synthesis of PPy-CO$_2$.

PPy-$CO_2$ can be produced, for example, according to the scheme depicted in FIG. 12, in which pyrrole is functionalized with $CO_2$ to produce the monomer 1H-pyrrole-1-carboxylic acid which is then polymerized. As demonstrated in the examples herein, PPy-$CO_2$ is capable of extracting metals and even rare earth elements. (FIGS. 19-20.) Similar to PPy-$CS_2$, a method of extracting metals with PPy-$CO_2$ may involve chelation instead of adsorption. The PPy-$CO_2$ may form a chelation complex with a metal ion as shown in Formula V:

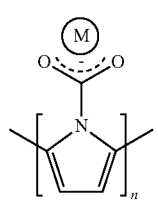

Formula V where M is a metal cation comprising a metal selected from the group consisting of Be, Mg, V, Cr, Mn, Fe, Co, Ni, Cu, Zn, Ga, As, Se, Rb, Ag, Cd, Cs, Ba, Au, TI, Th, Pb, and U, or a rare earth element selected from the group consisting of La, Ce, Pr, Nd, Sm, Eu, Gd, Dy, Ho, Er, Tm, Yb, and Lu, and n is an integer greater than 1. $PPy-CO_2$ can be used in any manner as described above with respect to $PPy-CS_2$.

Figure 11:
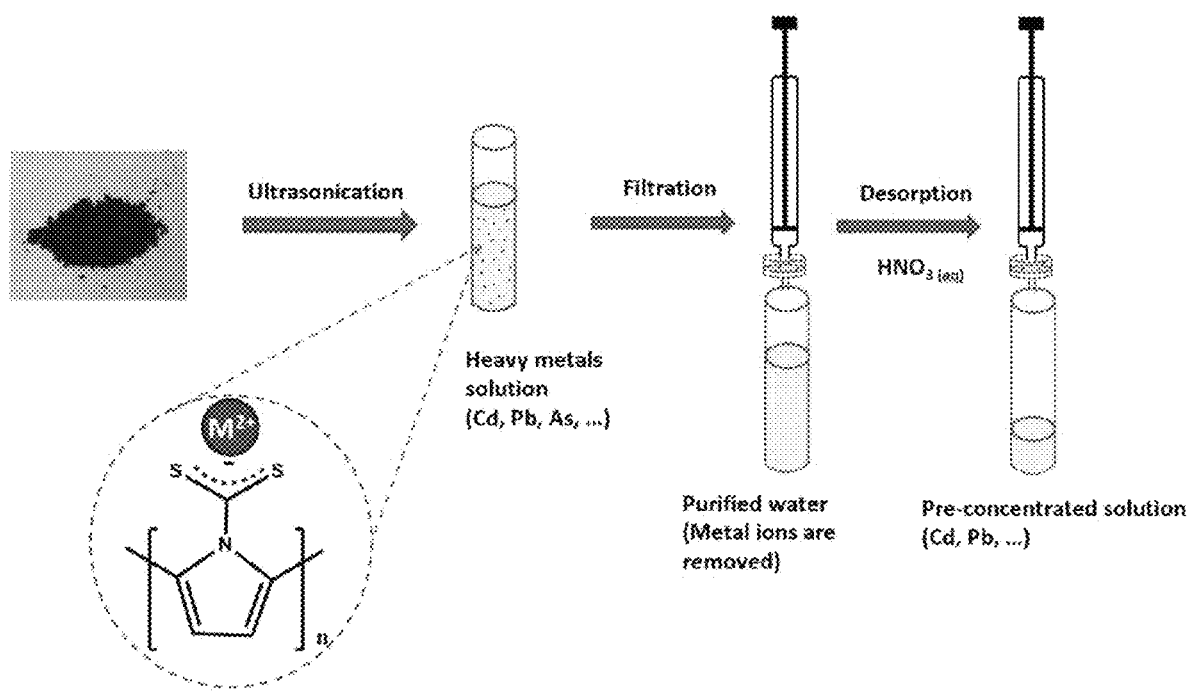
FIG. 11: Illustration of the general analysis protocol used in the examples herein.

In one non-limiting example method, $PPy-CS_2$ or $PPy-CO_2$ may be used to detect or quantify a metal, as depicted in FIG. 11, depicting $PPy-CS_2$ as an example. A composition comprising $PPy-CS_2$, $PPy-CO_2$, or a combination thereof may be dispersed into a solution containing a metal at a first concentration in order to chelate the metal. An agitation step may be conducted by any suitable method so as to uniformly disperse the $PPy-CS_2$, $PPy-CO_2$, or combination thereof in the solution. In some embodiments, ultrasound-assisted dispersion is utilized. Ultrasound disperses the polymer(s) quickly and makes the dispersion more uniform than other methods. If agitation is not conducted, the polymer(s) may settle to the bottom of the solution where it may not extract metal ions as efficiently. However, methods without an agitation step are nonetheless possible and encompassed within the scope of the present disclosure. Once dispersed, the solution contains $PPy-CS_2$, $PPy-CO_2$, or a combination thereof and chelation complexes between $PPy-CS_2$ or $PPy-CO_2$ and the metal. The solution may then be passed through a filter, such as a porous filter having a pore size of about 0.2 microns, in order to remove the $PPy-CS_2$ and/or $PPy-CO_2$, and chelation complexes, from the solution, producing a purified solution with metal ions removed. In the filtration step, the solution containing polymer(s) may be forced through a syringe filter. The polymer(s) may become trapped in the filter, resulting in a solution with metals removed by passing it through the filter. The filter may have a pore size of about 0.2 microns. However, the polymer(s) may be ground to reduce the particle size, in which case the filter may have pore size smaller than about 0.2 microns. Other filter sizes are nonetheless possible and encompassed within the scope of the present disclosure.

Desorption can be conducted using any acid. Without wishing to be bound by theory, it is believed that the polymers release the chelated metals by protonation of one of the sulfur atoms or oxygen atoms in the monomers. Thus, the filter, with the $PPy-CS_2$ polymer and/or $PPy-CO_2$ polymer trapped therein, may be rinsed with an acid such as $HNO_3$ so as to cause desorption of the metal from the $PPy-CS_2$ and/or $PPy-CO_2$ by protonation, producing a pre-concentrated solution of the metal having a second concentration of the metal which is greater than the first concentration. The pre-concentrated solution may then be analyzed as desired in order to detect and/or quantify the metal. However, many other methods utilizing $PPy-CS_2$ and/or $PPy-CO_2$ to detect and/or quantify metals are possible.

Figure 19A:
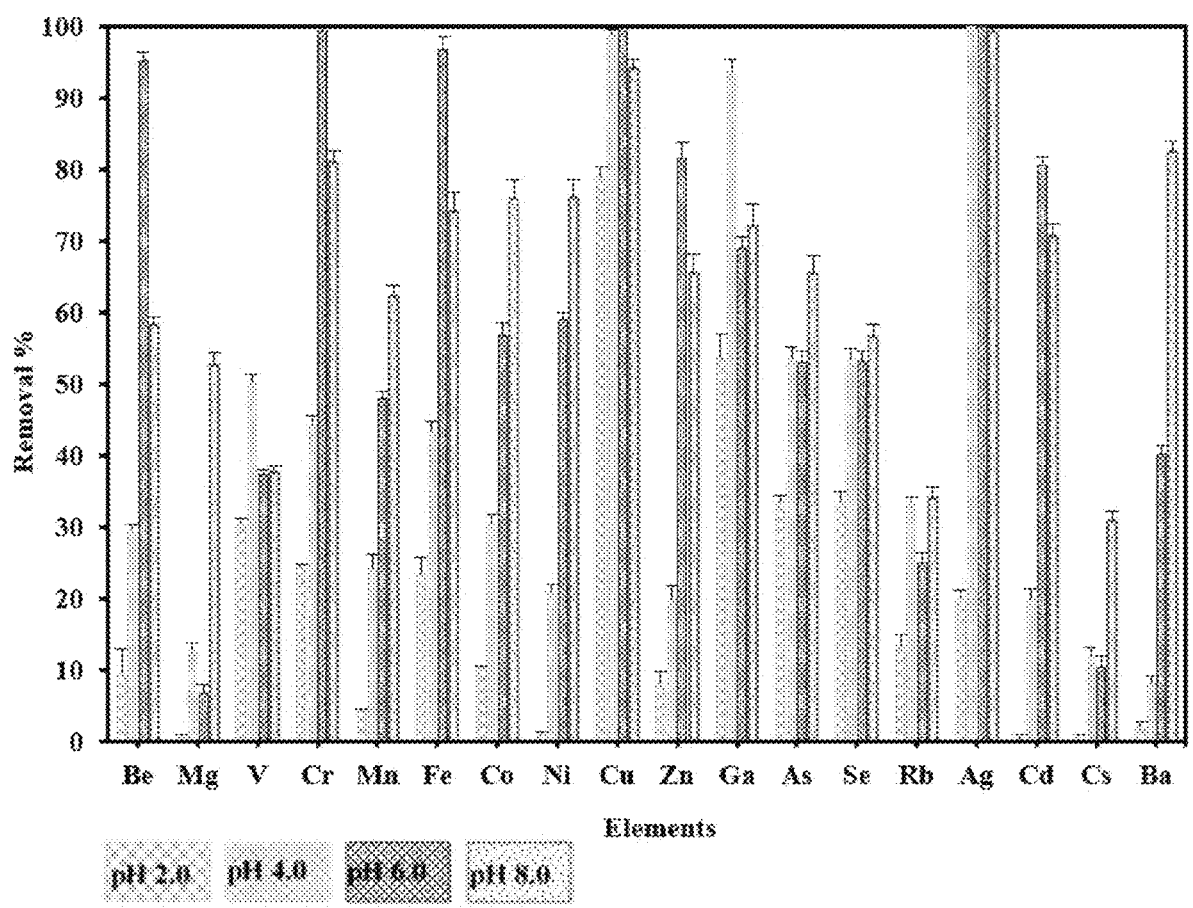
FIGS. 19A-19B: Removal % of Be, Mg, V, Cr, Mn, Fe, Co, Ni, Cu, Zn, Ga, As, Se, Rb, Ag, Cd, Cs, and Ba (FIG. 19A), and removal % of REEs, Au, Tl, Th, Pb, and U (FIG. 19B) from a multi-element solution of containing 250 μg L$^{-1}$ of each metal ions as a function of pH by PPy-CO₂. (Condition: amount of polymer: 10 mg, extraction time: 30 mins.)
Figure 19B:
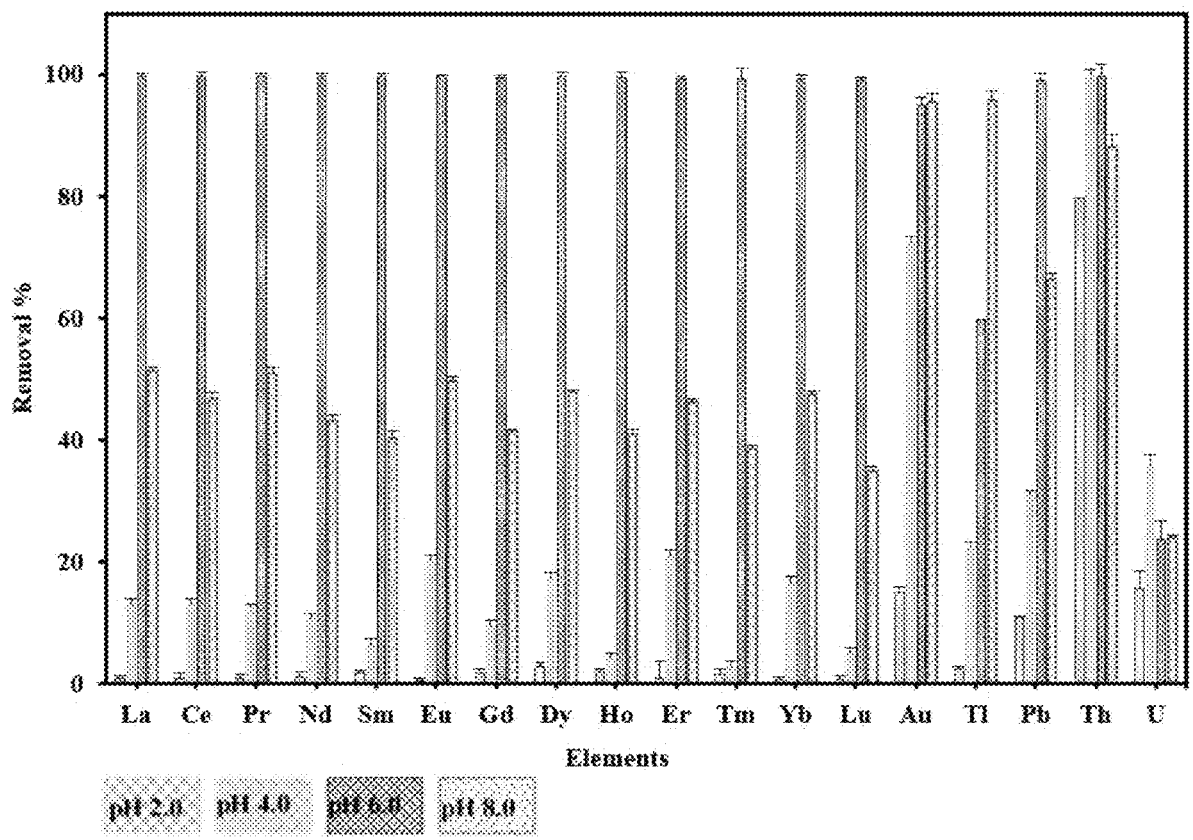
Figure 20A:
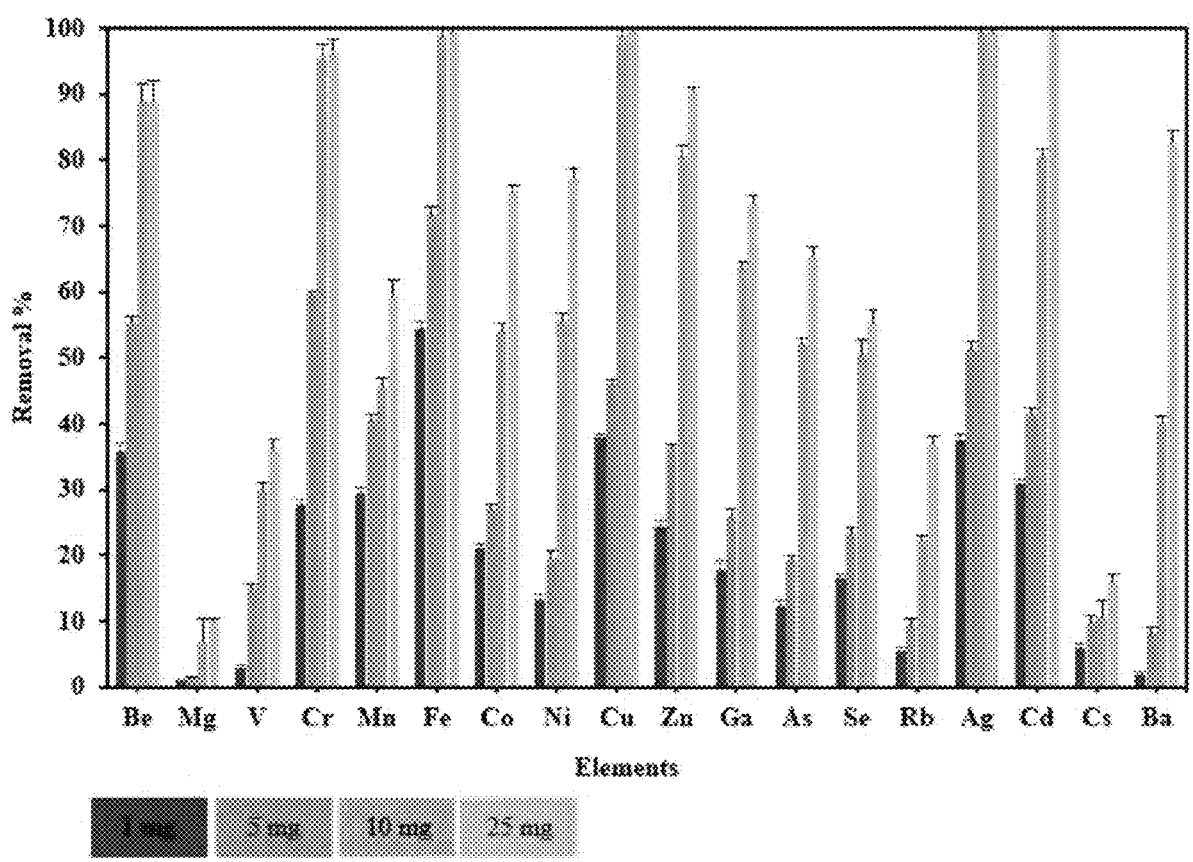
FIGS. 20A-20B: Removal % of Be, Mg, V, Cr, Mn, Fe, Co, Ni, Cu, Zn, Ga, As, Se, Rb, Ag, Cd, Cs, and Ba (FIG. 20A), and removal % of REEs, Au, Tl, Th, Pb, and U (FIG. 20B) from a multi-element solution of containing 250 μg L$^{-1}$ of each metal ions as a function of amount of PPy-CO₂ at pH 6.0.
Figure 20B:
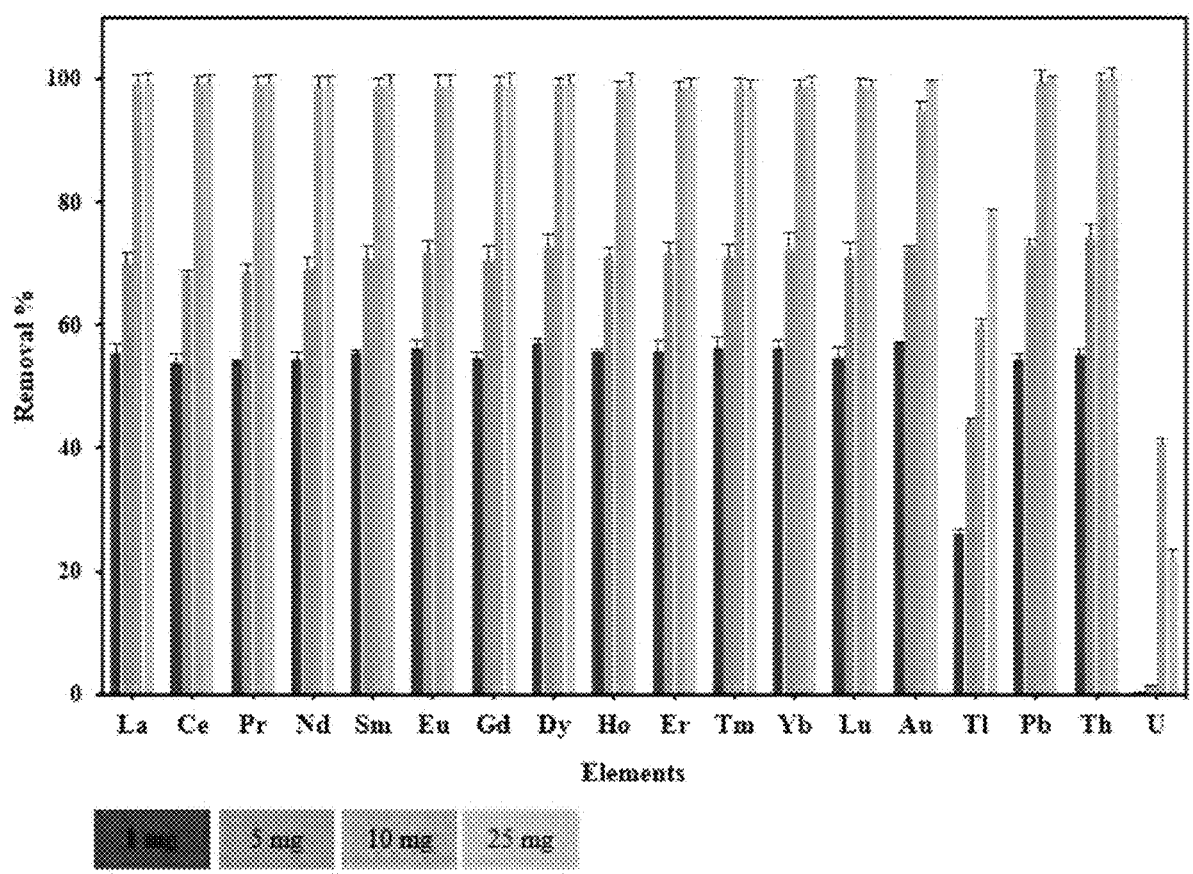

Surprisingly, as seen in FIGS. 6A-6B, 19A, 20A, $PPy-CS_2$ and $PPy-CO_2$ are each significantly better than PPy at extracting heavy metals. Furthermore, as seen in FIGS. 19B, 20B, $PPy-CO_2$ is useful for extracting rare earth elements. $PPy-CS_2$ and $PPy-CO_2$ may be used, individually or in combination, in selective extraction and microextraction devices, water purification systems, filters, columns, and the like. The polymers may be useful for the removal of hazardous contaminants from drinking water, wastewater, soil, or air, and for improved analytical testing. $PPy-CS_2$ and/or $PPy-CO_2$ may also be used to extract metal catalysts from reaction mixtures such as palladium, ruthenium, or iridium.

The $PPy-CS_2$ or $PPy-CO_2$ materials may be used in a variety of applications. A composition comprising $PPy-CS_2$, $PPy-CO_2$, or a combination thereof may be deposited on a substrate, such as a conductive or magnetic material or silica, to provide a sorbent material. A composition comprising $PPy-CS_2$, $PPy-CO_2$, or a combination thereof may be coated on a solid-phase microextraction (SPME) fiber for SPME analysis of metal analytes. A composition comprising $PPy-CS_2$, $PPy-CO_2$, or a combination thereof may be packed into a column for chromatographic analysis of metal analytes. A filter may be filled with a composition comprising $PPy-CS_2$, $PPy-CO_2$, or a combination thereof, including on a large scale so as to filter metals out of large areas of bodies of water. For example, a mesh bag may be filled with $PPy-CS_2$, $PPy-CO_2$, or a combination thereof and inserted into a river or lake so as to chelate metals out of the river or lake. Many other applications of the $PPy-CS_2$ and $PPy-CO_2$ materials are possible and encompassed within the scope of the present disclosure.

Though the extraction of metals is described herein for exemplary purposes, use of $PPy-CS_2$ and/or $PPy-CO_2$ is not limited to extracting or chelating metals. The polymers may be used in applications other than extracting metals. For instance, the polymers may be used to create a conductive film, such as in a semiconductor device to avoid pin holes or in a battery as a conductive contact.

It is further envisioned that the compositions and methods described herein may be embodied in the form of a kit or kits. A non-limiting example of such a kit may include a composition comprising Formula A in a first container, and one or more of an acid, a syringe, or a filter in a second container, where the containers may be present in a combined configuration or package. Many other kits are possible. The kits may further include instructions for using the components of the kit to practice the subject methods. The instructions for practicing the subject methods are generally recorded on a suitable recording medium. For example, the instructions may be present in the kits as a package insert or in the labeling of the container of the kit or components thereof. In other embodiments, the instructions are present as an electronic storage data file present on a suitable computer readable storage medium, such as a flash drive. In other embodiments, the actual instructions are not present in the kit, but means for obtaining the instructions from a remote source, such as via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

Sorbent materials were developed based on carbon disulfide ($CS_2$) or carbon dioxide ($CO_2$) functionalization of pyrrole and chemical polymerization of the respective monomers. The synthesized polymers, poly(1H-pyrrole-1-carbodithioic acid) ($PPy-CS_2$) and poly(1H-pyrrole-1-carboxylic acid) ($PPy-CO_2$), were utilized for a simple, sensitive, and fast ultra-trace extraction and determination of metals using ultrasound assisted dispersive micro solid-phase extraction (UAD μ-SPE). In this technique, the $PPy-CS_2$ or $PPy-CO_2$ polymer was dispersed in water samples containing metal ions with the aid of ultrasonic agitation. After extraction of the metals by the polymer, the polymer was filtered and the metal ions were desorbed into a smaller volume for analysis by inductively coupled plasma-mass spectrometry (ICP-MS). PPy-CS$_2$ and PPy-CO$_2$ were evaluated to extract divalent and trivalent heavy metals including Cd(II), Co(II), Cu(II), Ni(II), Pb(II), and Zn(II). Excellent removal and recovery efficiency for the metal ions compared to the unfunctionalized polypyrrole (PPy) polymer was demonstrated. The influence of the experimental parameters affecting extraction efficiency including pH, extraction time, and the flow rate of desorption solution were evaluated. The method was also successfully applied for evaluating the metal ion content in real water samples.

Example I

Instrumentation

All the samples were analyzed for metal ion determination using an inductively coupled plasma mass spectrometer (Thermo Scientific XSereies 2) equipped with a slurry nebulizer. The m/z values of $^{75}$As (74.9216), $^{111}$Cd (110.9042), $^{59}$Co (58.9332), $^{65}$Cu, $^{60}$Ni (59.9308), $^{208}$Pb (207.9766), and $^{66}$Zn (65.9260) were used to quantify each metal. The ICP-MS instrumental parameters are shown in Table 1. A Fourier transform infrared (FTIR) spectrometer (PerkinElmer Frontier spectrometer, Shelton, Conn.) was used in the attenuated total reflectance (ATR) mode. Measurements of pH were done using a Basic pH Meter (Denver Instrument Company, Denver, Colo.). A scanning electron microscope (JEOL JSM-7500F, JEOL USA, Inc., Peabody, Mass.) equipped with a BRUKER XFlash 5010 series energy dispersive X-ray spectroscopy (EDS) detector (Billerica, Mass.) was used to obtain scanning electron microscopy (SEM) images and EDS spectra. Gas chromatographic (GC-MS) analysis was performed using an Agilent Technologies GC-MS (Santa Clara, Calif.) consisting of a 7890 gas chromatograph coupled to a 5975C inert XL MSD with a Triple-Axis detector. NMR spectra were acquired using an Avance III 600 MHz spectrometer. Spectrophotometric characterizations were performed with an Evolution™ 300 UV-Visible spectrophotometer (Thermo Scientific, San Jose, Calif.) from 250-500 nm.

TABLE 1

| ICP-MS parameters | |
|---|---|
| Instrument | Thermo X Series 2 |
| RF power | 1400 W |
| Auxiliary flow, L min − 1 | 0.70 |
| Nebulizer gas flow, L min − 1 | 0.85 |
| Interface | Ni sample cone (1.1-mm orifice) Ni skimmer cone (0.75-mm orifice) |
| Measured isotopes | $^{75}$As, $^{111}$Cd, $^{59}$Co, $^{65}$Cu, $^{60}$Ni, $^{208}$Pb, and $^{66}$Zn |
| Dwell time, ms | 600 |
| Duration time, sec | 120 |
| No. of replicates per sample | 4 |
| Internal Standardization | Li, Sc, In, Y, Bi with interpolation. |
| Technique | |
| Carrier solution | 3.5% HNO$_3$ (trace metal grade) |

Reagents and Solutions

All chemicals were of analytical grade and used as received. Water from a Barnstead B-pure water purification system (>17 MΩ cm) was used for the preparation of all aqueous solutions. The pH was adjusted by using dilute nitric acid and sodium hydroxide. Nitrate salts of As, Cd, Co, Cu, Ni, Pb, and Zn were purchased from Fisher Scientific with highest purity available and used for preparation of stock solutions. Ferric chloride (FeCl$_3$) and ammonium persulfate (APS) (Fisher Scientific) were purchased and used as oxidizing agents.

Pyrrole (Sigma Aldrich, Milwaukee, Wis.) was distilled before each use. Carbon disulfide (CS$_2$) and sodium hydride (NaH, 60% dispersion in mineral oil) were purchased from Oakwood Chemicals (Estill, S.C.) and Acros Organics (Morris Plans, N.J.), respectively. Acrodisc minispike syringe filters from Sigma Aldrich (PTFE membrane, pore size 0.2 μm) were used for sample filtration. All the glassware was kept in 1 M HNO$_3$ solution and washed with deionized water prior to solution preparation. A high purity drinking water standard (CRM-TMDW, High-Purity Standards, North Charleston, S.C.) was utilized as a certified reference material.

Synthesis of Py-CS$_2$ and PPy-CS$_2$

The scheme shown in FIG. 1A depicts the synthesis of the pyrrole-based monomer, 1H-pyrrole-1-carbodithioic acid, and the corresponding polymer after chemical polymerization. The resulting polymer was a dark fine powdered solid material (FIG. 1B), easily weighed and handled.

Figure 9:
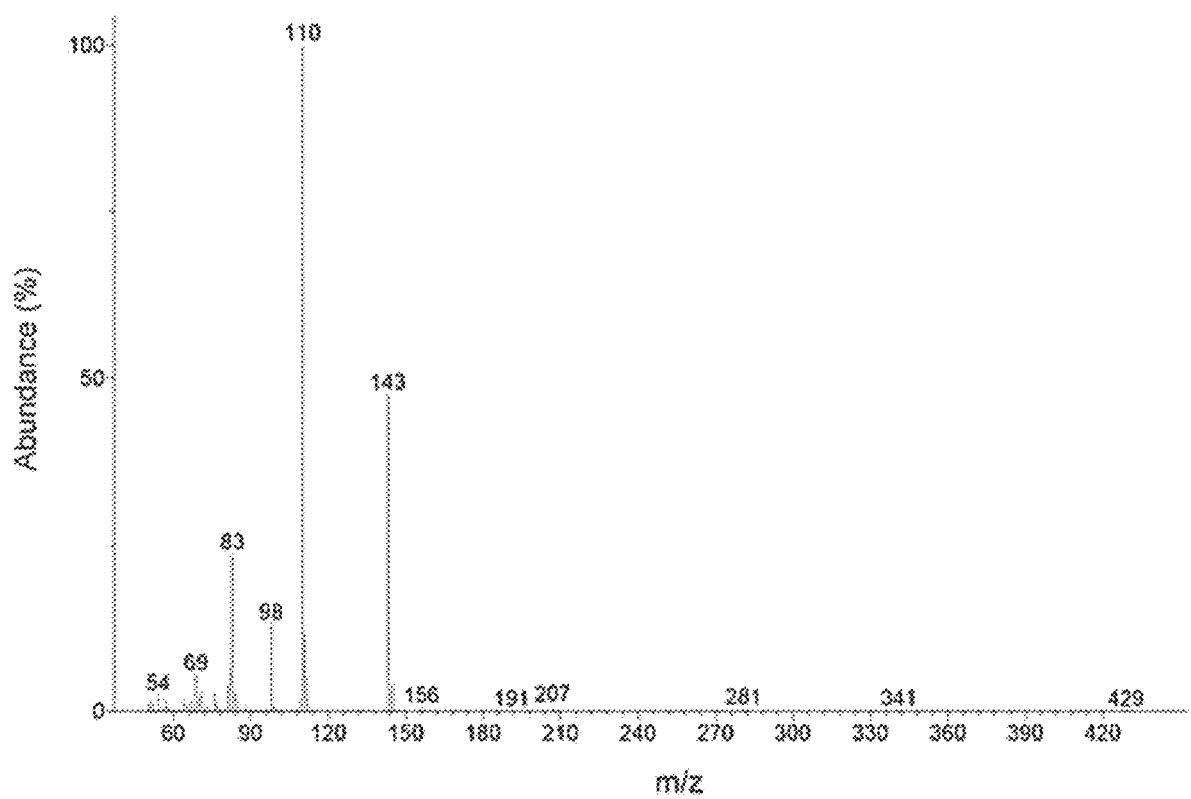
FIG. 9: Mass spectrum of the synthesized Py-CS$_2$.

The synthetic procedure for preparation of 1H-pyrrole-1-carbodithioic acid is given below (FIG. 1A). 1.39 mL of pyrrole (0.02 mol) was added dropwise to a stirred solution of sodium hydride (60% dispersion in mineral oil, 0.8 g, 0.02 mol) in dimethyl sulfoxide (10 mL). The resulting solution was then cooled in an ice water bath. Next, 1.21 mL of carbon disulfide (0.02 mol) was introduced at a flow rate of 1.4 mL h using a model 220 series syringe pump (KD Scientific, MA, USA). A deep red solution of poly(1H-pyrrole-1-carbodithioic acid) was obtained and stored under nitrogen at 5° C. The product solution was extracted with diethyl ether (3×5 mL) to remove the unreacted pyrrole. Then, 1 M aqueous hydrochloric acid was added dropwise to acidify the solution, which was then extracted with diethyl ether (2×10 mL) solution. The combined ether extracts were dried over anhydrous sodium sulfate and used for GC-MS, NMR, and FTIR characterization. Any attempt to isolate pure product by evaporation, condensation, or crystallization leads to the formation of aggregates or oxidation products. Therefore, the monomer was stored in either the diethyl ether solution or in dimethyl sulfoxide solution for the characterization and subsequent polymerization step, respectively. $^1$H NMR (600 MHz, CDCl$_3$): δ (ppm) 7.61 (m, 2H), 6.33 (m, 2H), 1.54 (S, 1H). MS m/z [M]$^+$: 143 (FIG. 9).

To prepare the corresponding PPy-CS$_2$ polymer, FeCl$_3$ or APS were used as an oxidation agent. An acid washing step of the polymer was conducted if FeCl$_3$ was the oxidation agent since the remaining iron ion in the polymer can interfere with other metal ions. To eliminate this acid washing step, APS was also used in this example. After preparation of the monomer, a 10 mL (0.02 mol) of Py-CS$_2$ was placed in a round bottom flask. Then, 9.13 g APS (0.04 mol) in 20 mL of deionized water was introduced at the rate of 10 mL h using syringe pump. The reaction mixture was kept overnight under stirred condition at room temperature to complete the polymerization step. Next, the polymer was separated from excess reagents and solvents by using vacuum filtration and washed several times with 1M HCl solution ethanol, and deionized water. A dark black powder of PPy-CS$_2$ was air dried and stored at room temperature.

General Extraction Procedure

FIG. 11 illustrates the general analysis protocol used in this example. To extract heavy metals (FIG. 2), 5 mg of the synthesized polymer was first dispersed in a 10 mL solution containing 250 μg L$^{-1}$ of each metal ions using an ultrasonic bath to aid the dispersion. The stable dispersed mixture was left for 5 min to complete the sorption of metal ions to the polymer. Then, the dispersed solution was carefully transferred to a 12 mL syringe and filtered using a 0.2 μm syringe filter (PTFE membrane, pore size 0.2 μm). The remaining solution was saved for ICP-MS analysis and the filtered polymer was washed with deionized water and then 1 mL of 2 M nitric acid solution to perform the metal desorption step. The eluted solution was also used for ICP-MS analysis to obtain the recovery of the UAD μ-SPE procedure.

In these experiments, the efficiency of heavy metal removal was calculated according to the following equation:

$$\text{Removal efficiency \%} = \frac{C_0 - C_e}{C_0} \times 100$$

where $C_0$ is the initial concentration (μg $L^{-1}$) and $C_e$ is the remaining concentration (μg $L^{-1}$) of sample solution at equilibrium after extraction and filtration. The extraction recovery was calculated based on the percentage of the total metal ion ($n_0$) eluted in the desorption solution ($n_f$):

$$\text{Extraction Efficiency \%} = \frac{n_f}{n_0} \times 100 = \left(\frac{C_f \times V_f}{C_0 \times V_0}\right) \times 100$$

where $C_f$ and $V_f$ are the final concentration and volume of the desorbed solution, respectively. The relative recovery was also calculated according to the following equation:

$$\text{Relative recovery \%} = \frac{C_{found} - C_{real}}{C_{spiked}} \times 100$$

where $C_{found}$ is the concentration of metal ion after addition of known amount of standard solution to real sample, $C_{real}$ is the concentration of metal ion in real sample, and $C_{spiked}$ is the concentration of standard solution that was spiked into real samples.

Results and Discussion

The PPy-$CS_2$ polymer was designed for the effective extraction of metal ions from water. The polymer incorporates carbodithioic acid, a bidentate chelating functional group, into a conducting polymer backbone to provide a material that extracts metals by a chelation mechanism, which is much stronger and more selective than extraction by adsorption. Carbodithioic acid has several beneficial characteristics. First, sulfur is a soft electron donor atom with a strong affinity toward specific divalent transition metals, which are relatively soft cations. In comparison to dithiocarbamate, which is a well-studied chelating ligand for hard and soft metals due to formation of dithiocarbamate and thioureide tautomers, carbodithioic acid is much more selective and preferentially chelates soft metal cations. An additional important characteristic is the dual functionality for deprotonation and protonation that allows for facile extraction and desorption of metal ions. Carbodithioic acid can be deprotonated at neutral pH and the electrostatic attraction between the negatively charged carbodithioate anion and the positively charged metal cations enhances chelation and, therefore, results in more efficient extraction. However, in acidic conditions, the carbodithioate group can be protonated or neutral, which releases or desorbs the metal ions for ease of analysis and reuse of the polymer. In effect, chelation in PPy-$CS_2$ is reversible. Therefore, the polymer can be recycled, provides fast extraction and recovery of metal ions, and ultimately results in a more environmentally friendly extraction approach.

Characterization of PPy-$CS_2$ Sorbent Material

Figure 3A:
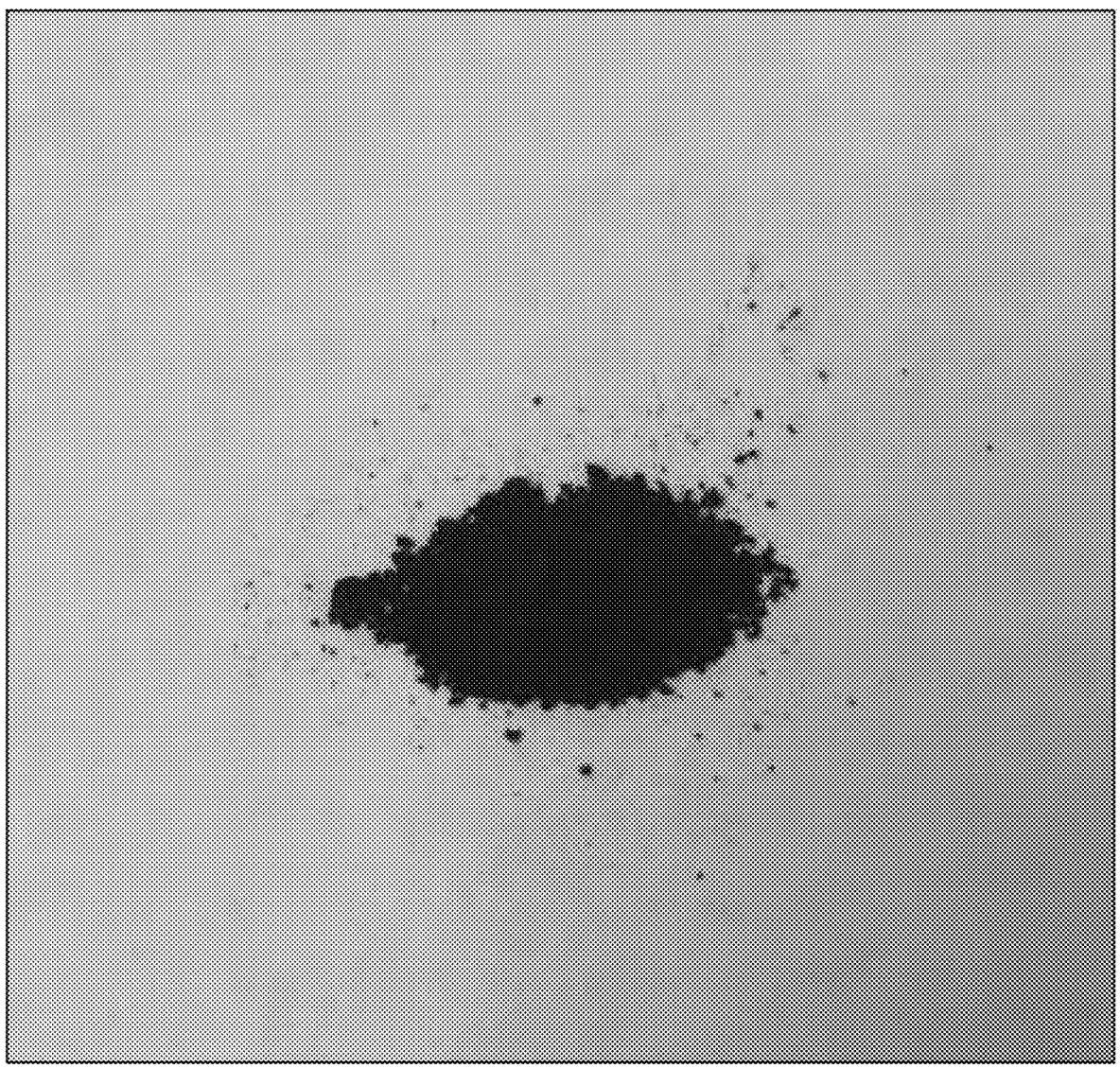
FIGS. 3A-3C: Photograph of the bulk material (FIG. 3A), SEM micrograph of synthesized polymer of PPy-CS$_2$ at low magnification (140×) (FIG. 3B), and SEM micrograph at high magnification (9,000×) for particle size estimation (FIG. 3C).
Figure 3B:
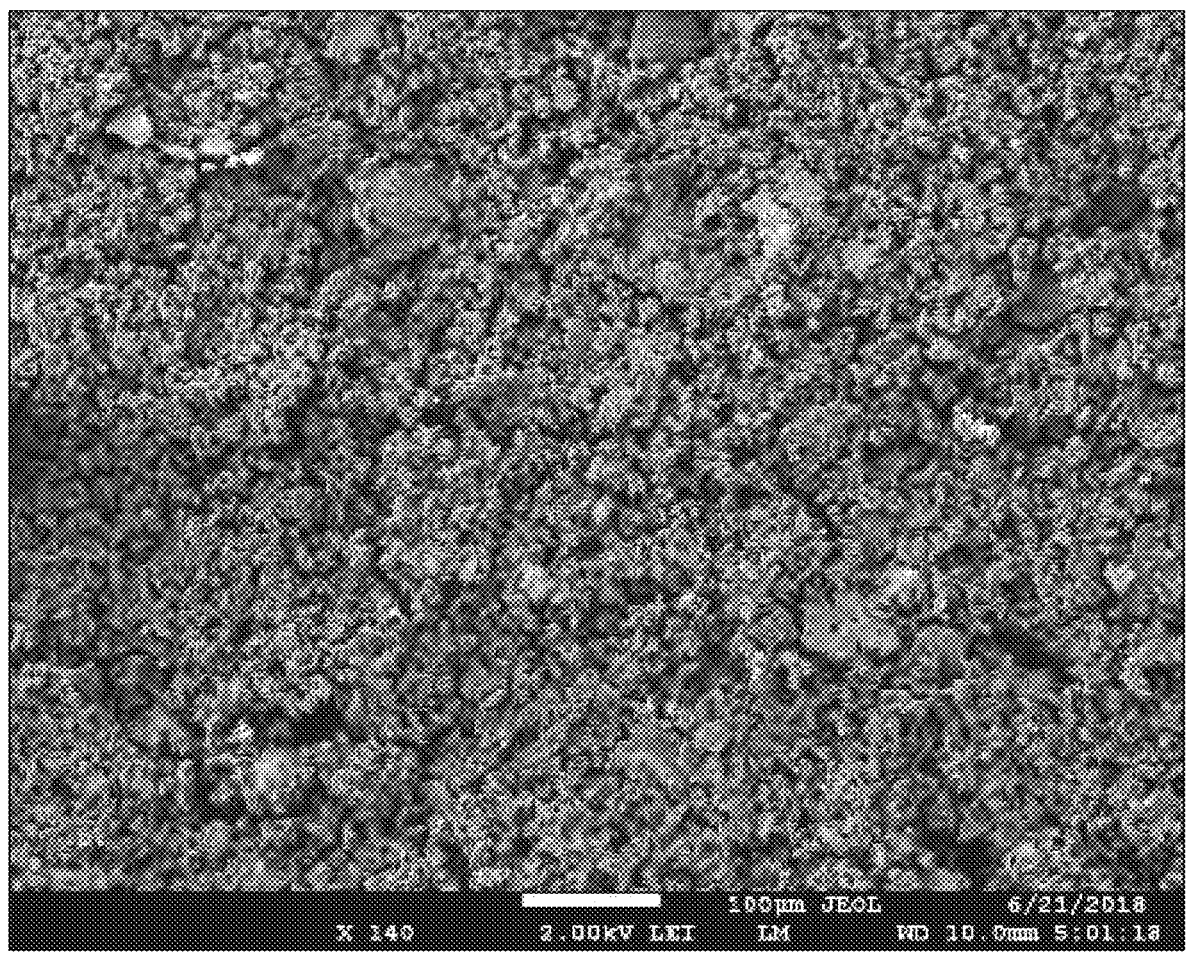

N-functionalization of pyrrole with carbodithioic acid readily produces the monomer, 1H-pyrrole-1-carbodithioic acid. Upon chemical polymerization, PPy-$CS_2$ is formed as a dark, air stable, black powder. SEM and EDS images also were used to further characterize the PPy-$CS_2$ polymer and explore the topography of the sorbent surface. SEM and EDX images are presented in FIGS. 3B-3C. The photograph of the bulk PPy-$CS_2$ polymer (FIG. 3A) and the SEM image (FIG. 3B) illustrate the granular nature and porosity of the material. This feature is useful because it causes higher extraction efficiency as well as faster kinetics of the extraction for the sorbent due to the large surface area and more functional chelating group available in the particles.

Figure 3C:
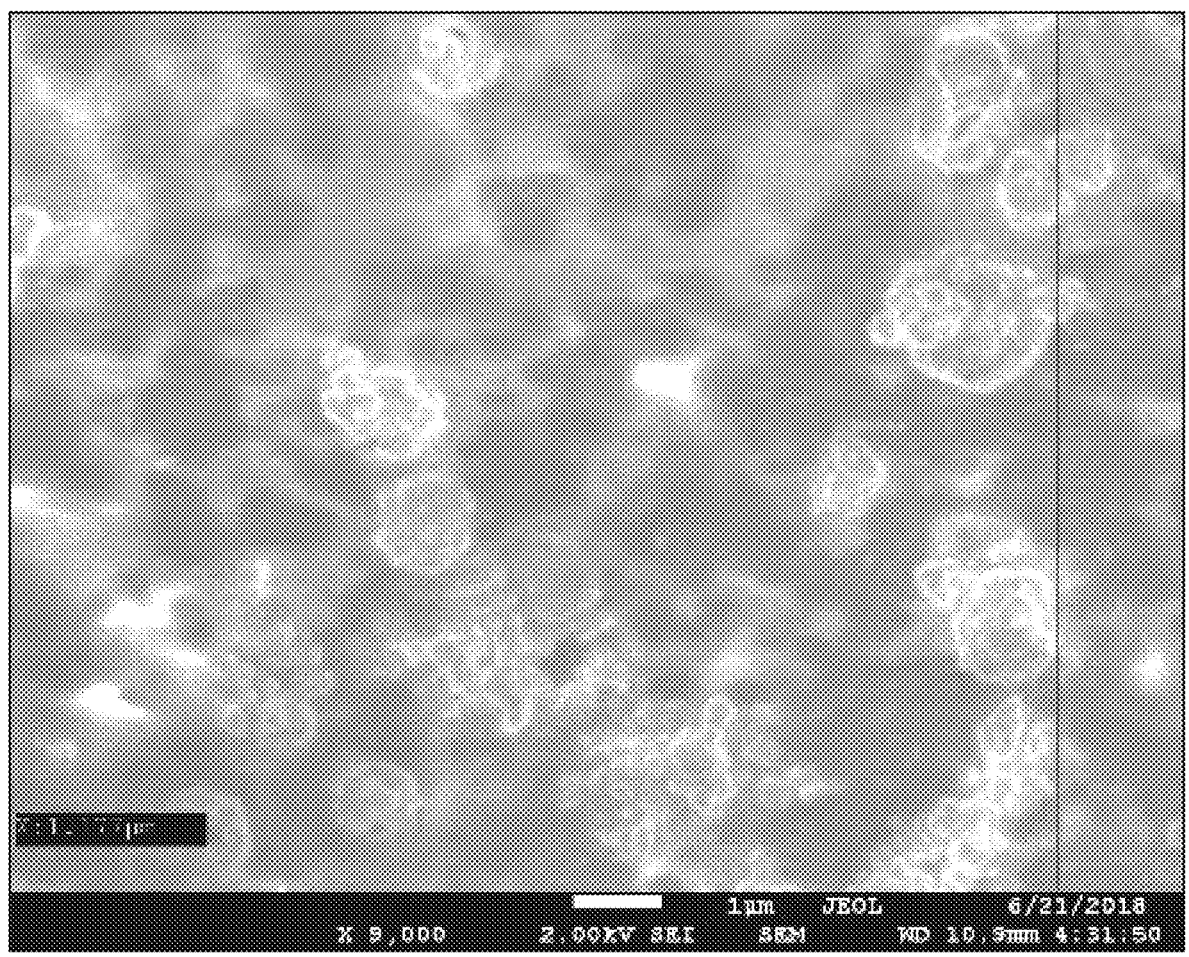
Figure 4A:
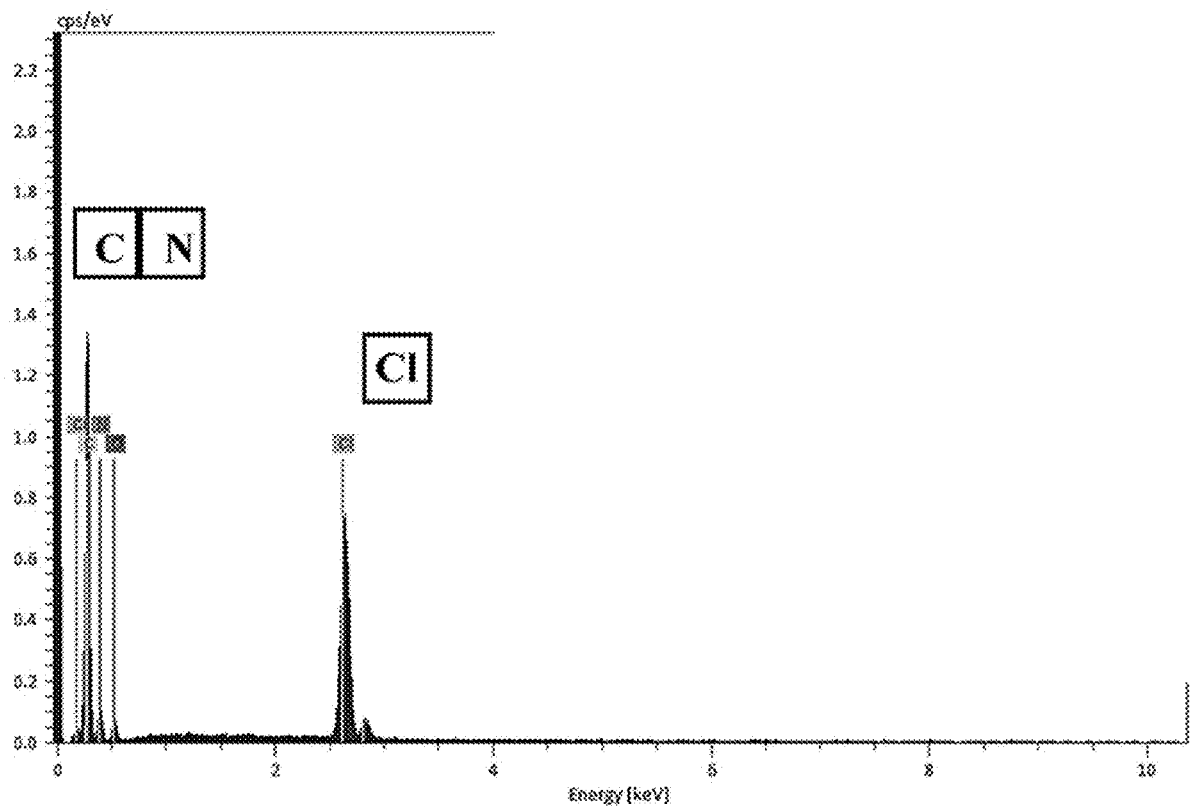
FIGS. 4A-4C: SEM-EDS spectrum of PPy (FIG. 4A), PPy-CS$_2$ (FIG. 4B), and PPy-CS$_2$ (FIG. 4C) after sorption of heavy metals.
Figure 4B:
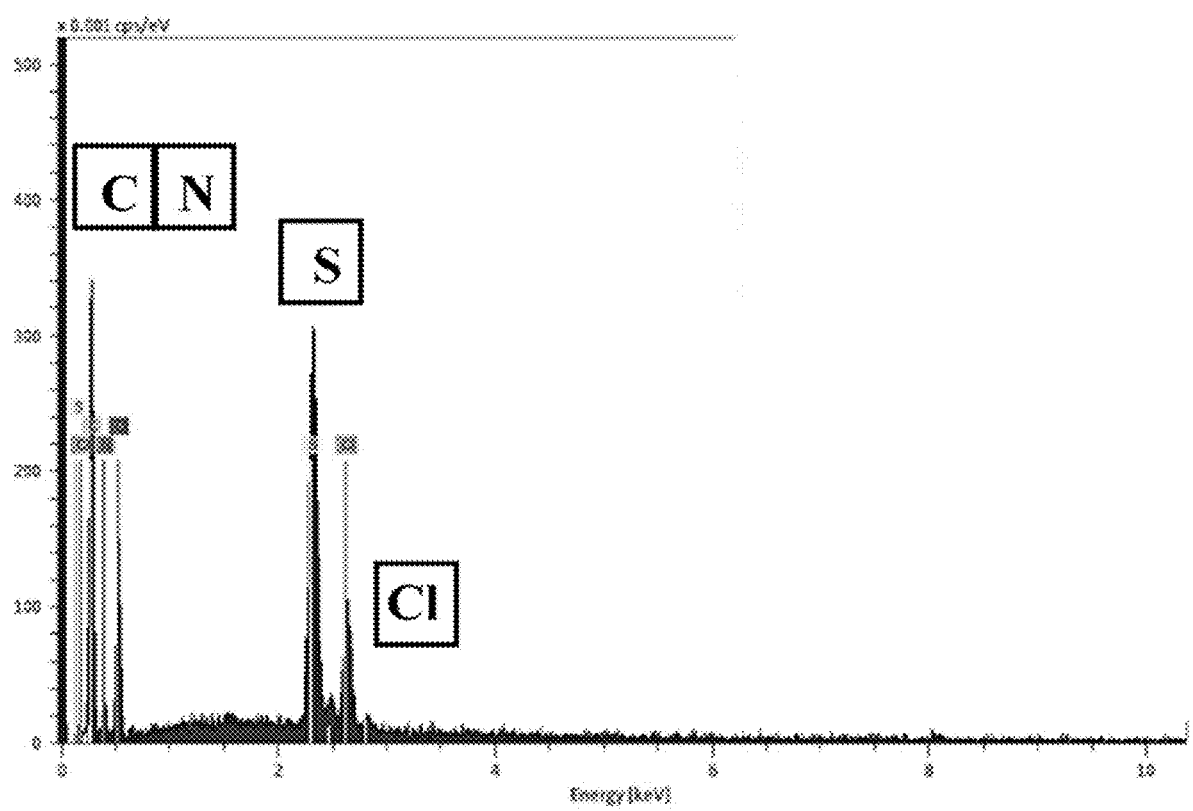
Figure 4C:
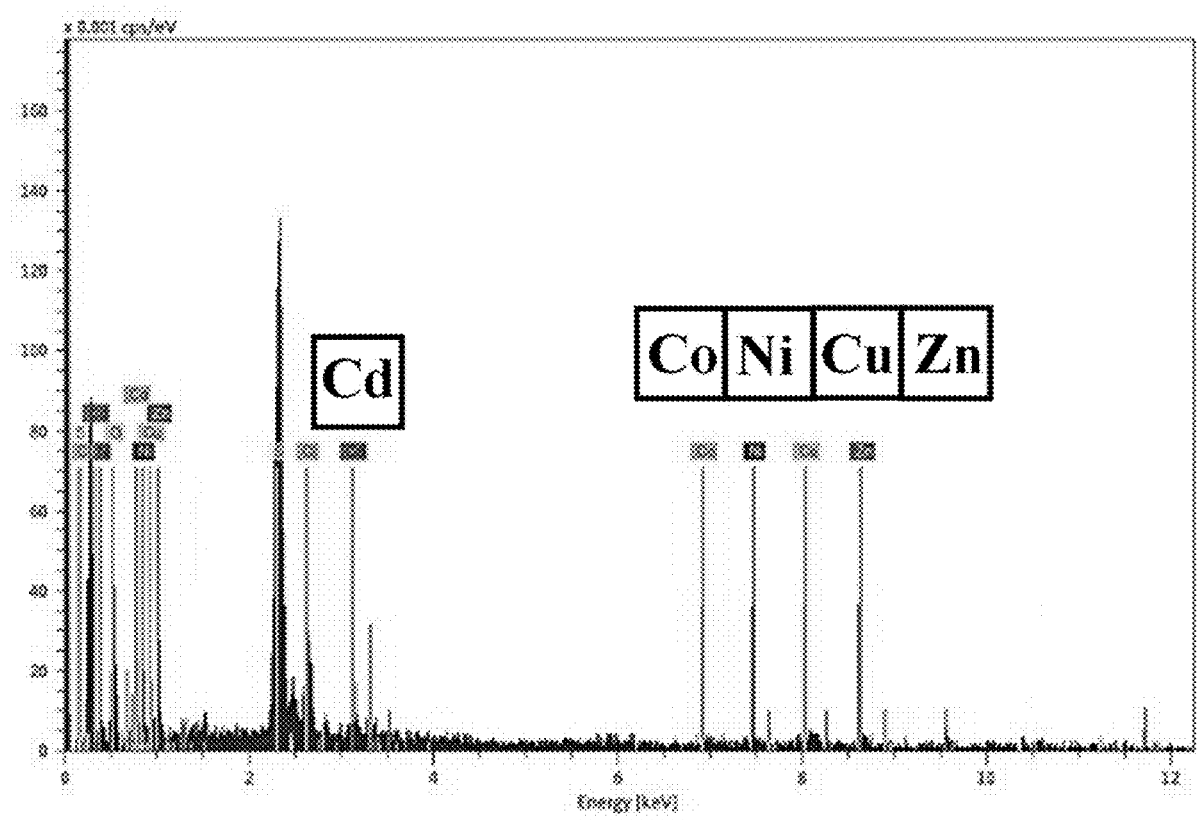

The particle size of the synthesized sorbent was estimated using FIG. 3C and other SEM images to be in the range of 1.1-1.9 μm. Based on the result, 0.2 μm syringe filters were used in the extraction experiments to allow complete separation of sorbent particles from sample solution. Particles were not observed after filtration in this case. FIGS. 4A-4C depict the EDX spectra of PPy, PPy-$CS_2$, and PPy-$CS_2$ after sorption of the heavy metals. A comparison of FIG. 4A to FIG. 4B clearly shows the presence of S atoms in PPy-$CS_2$ whereas in PPy, only C and N atoms peaks are present in the spectrum. The EDS spectrum of the polymer after extraction of heavy metals show peaks of all the corresponding metals which are small due to their low concentration in the extracted solution.

Figure 5A:
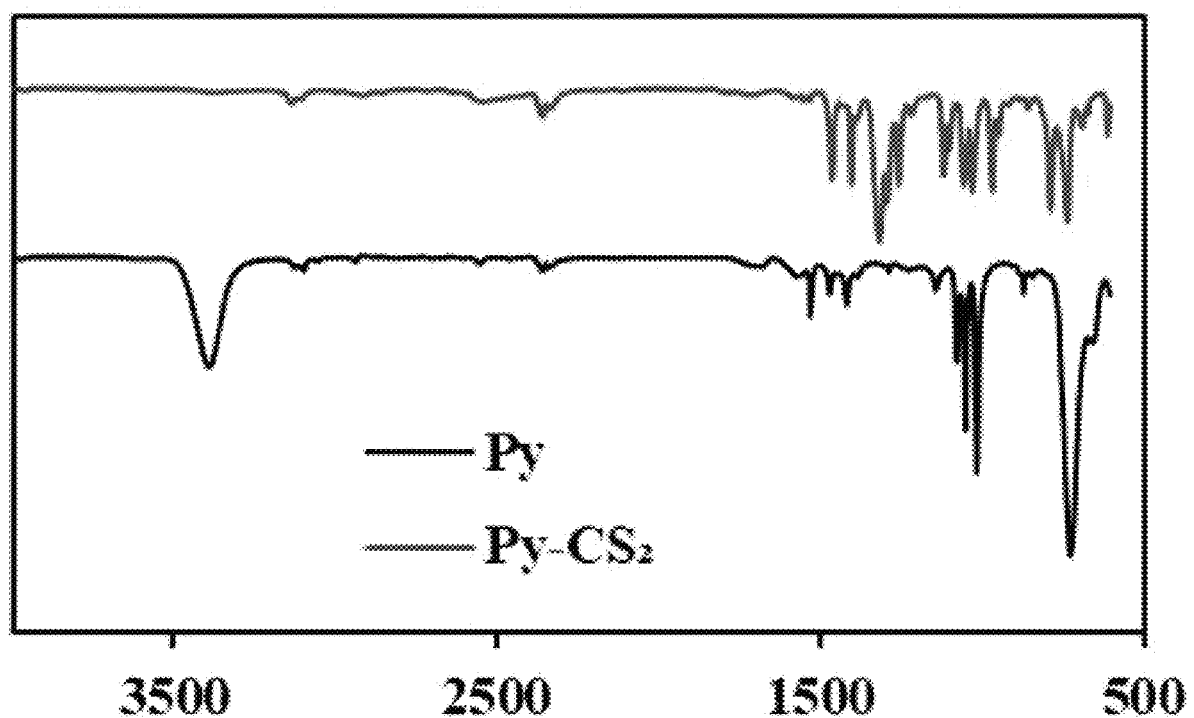
FIGS. 5A-5B: FTIR spectra of monomers Py and Py-CS$_2$ (FIG. 5A), and corresponding polymers PPy and PPy-CS$_2$ (FIG. 5B).
Figure 5B:
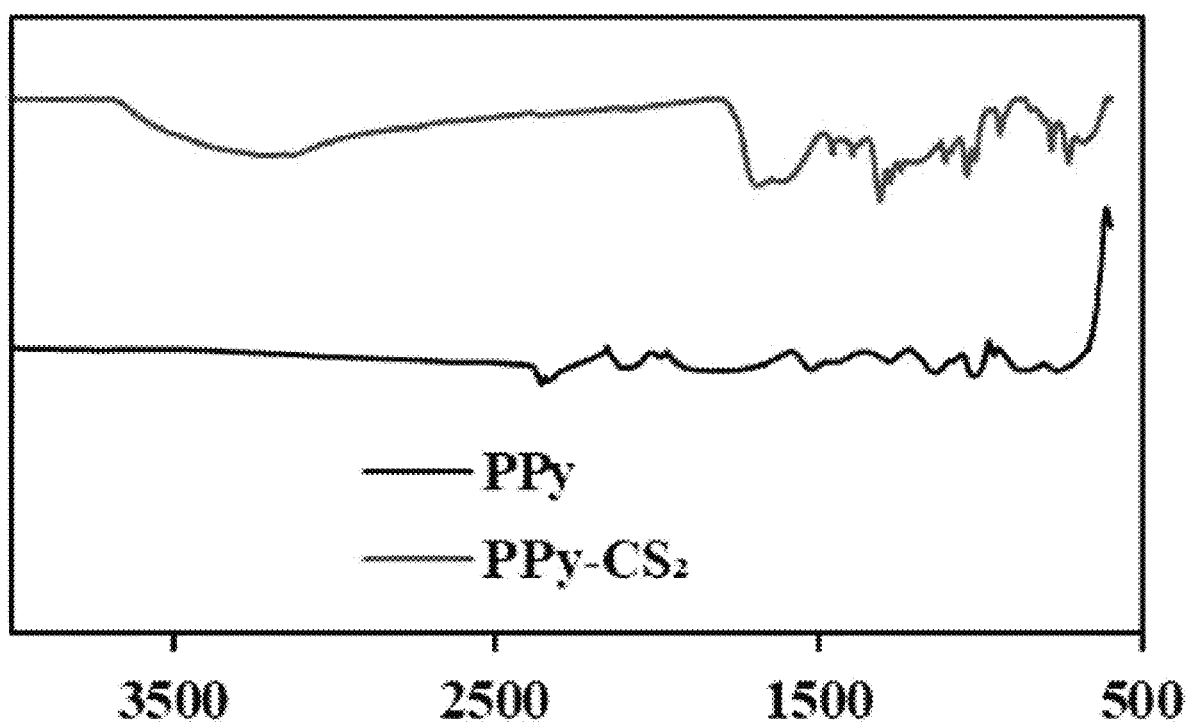

The PPy-$CS_2$ sorbent material particles were also examined by FTIR analysis and compared to unfunctionalized PPy (FIGS. 5A-5B). In these two spectra, the characteristic polypyrrole absorption band near 1550 and 1470 $cm^{-1}$ are due to the presence of C=C stretching, peaks around 1306 represent C—N bond, and 1007 $cm^{-1}$ correspond to =C—H out-of-plane vibrations. Moreover, the C=S absorption bands in PPy-$CS_2$ appear near 1290 $cm^{-1}$, which is absent in the PPy spectrum.

Figure 10A:
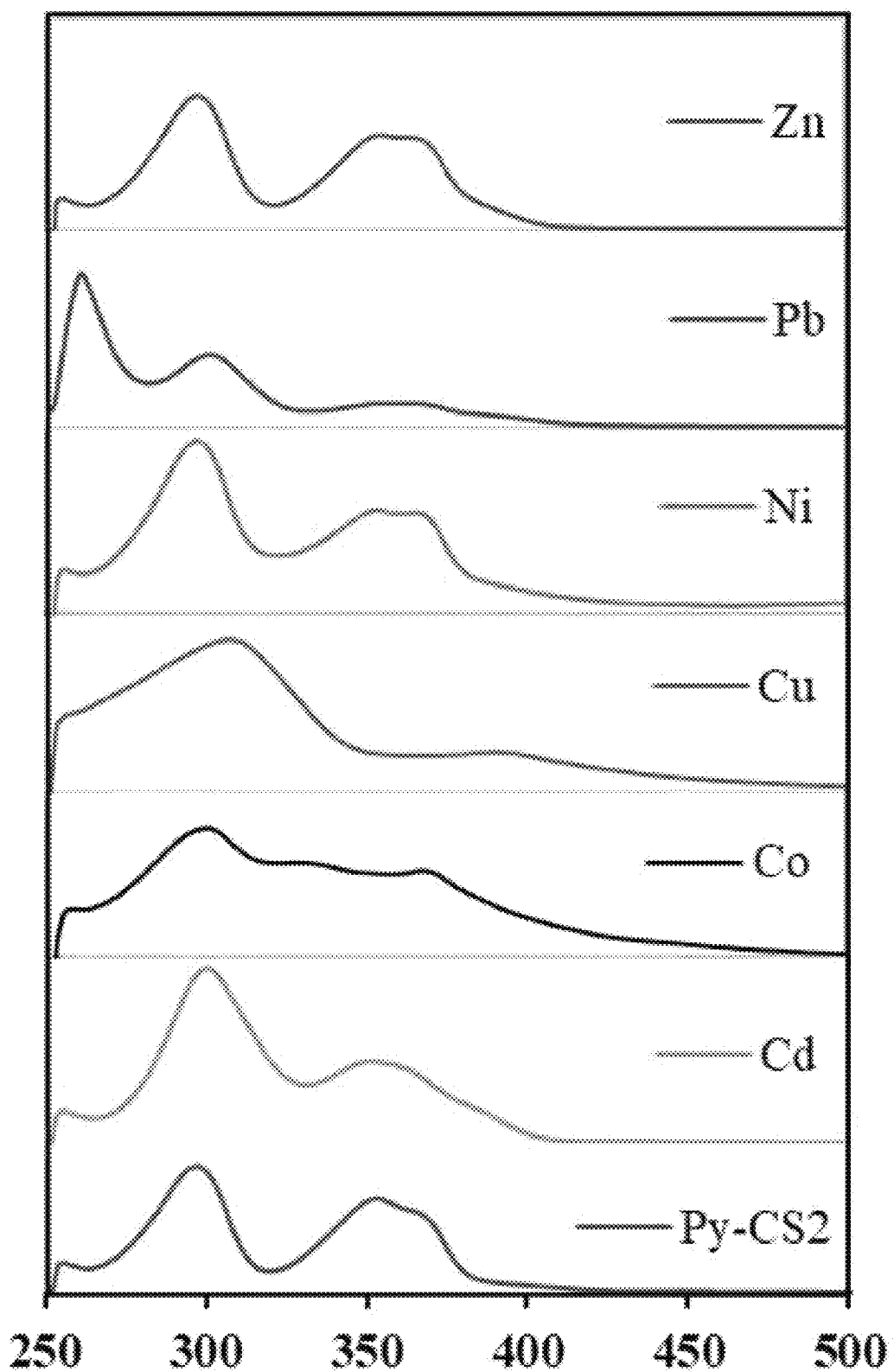
FIGS. 10A-10B: UV-Visible spectra of Py-CS$_2$ and its complexes with the heavy metals (FIG. 10A), and photograph showing the solutions of the complexes of Py-CS$_2$ monomer with Pb, Cd, Cu, Zn, Ni, and As in DMSO as solvent and mole ratio of 1:1 (FIG. 10B).
Figure 10B:
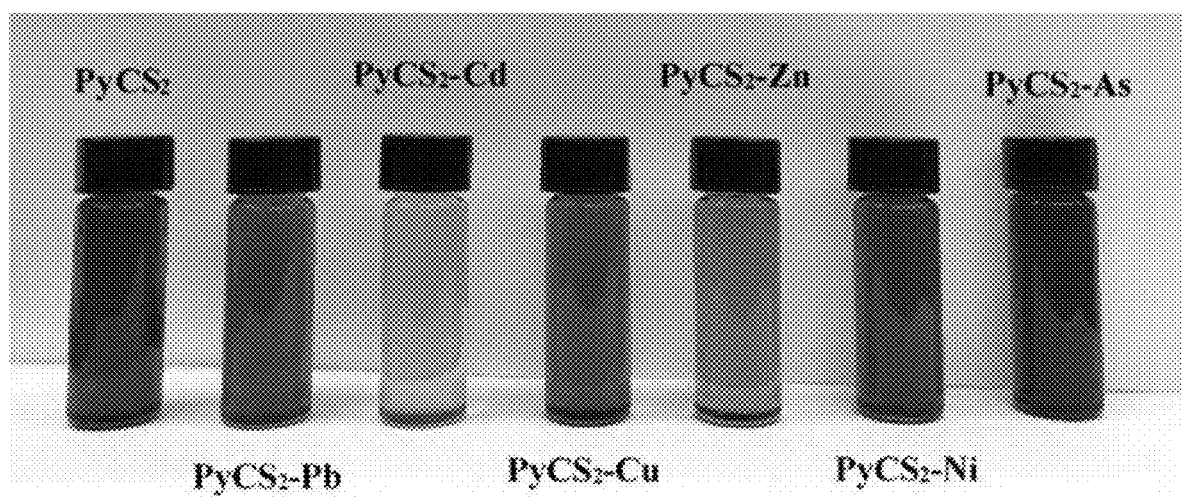

In preliminary experiments, color changes and precipitation reactions were utilized to investigate whether chelation of the monomer to the metals and therefore, the polymer, would be possible. When Py was added to aqueous solutions of Cd, Co, Cu, Ni, Pb, and Zn, no observable color changes were apparent, indicating complexation between the Py monomer and the metals likely did not occur. In contrast, immediate precipitation resulted after mixing an aqueous solution of the metals with the Py-$CS_2$ monomer, showing that the Py-$CS_2$ monomer forms complexes with Cd, Co, Cu, Ni, Pb, and Zn. Further confirmation of the complexation between the metal ions and Py-$CS_2$ was obtained by preparing a 1:1 mole ratio solution of each metal ion with the monomer in DMSO to solubilize any complex formed. An instant color change was observed after mixing the metal ions with the Py-$CS_2$ monomer without precipitation. The UV-visible spectra of the Py-$CS_2$ monomer-metal ion solutions are shown in FIG. 10A. Changes in the absorption spectra of the metal complexes compared to the Py-$CS_2$ ligand spectrum confirm chelation to each metal ion occurs. The shifts in absorption maximum in the spectra of the metal complexes compared to spectra of the ligand, clearly show the chelation of the monomer to each metal ions.

The complexation between As (V) and Py-$CS_2$ monomer was examined to show the selectivity of the monomer.

Arsenic is considered a hard ion with an oxidation state of +5, and therefore, chelation of the soft sulfur donor in Py-$CS_2$ is less favorable. After adding As (V) to Py-$CS_2$ monomer solution, neither a color change nor precipitation were observed, indicating that no strong complexation resulted. Without wishing to be bound by theory, it is believed that this is due to the hardness of arsenic with a high oxidation state of 5 and softness of S in the monomer as the functional chelating atoms.

Figure 6A:
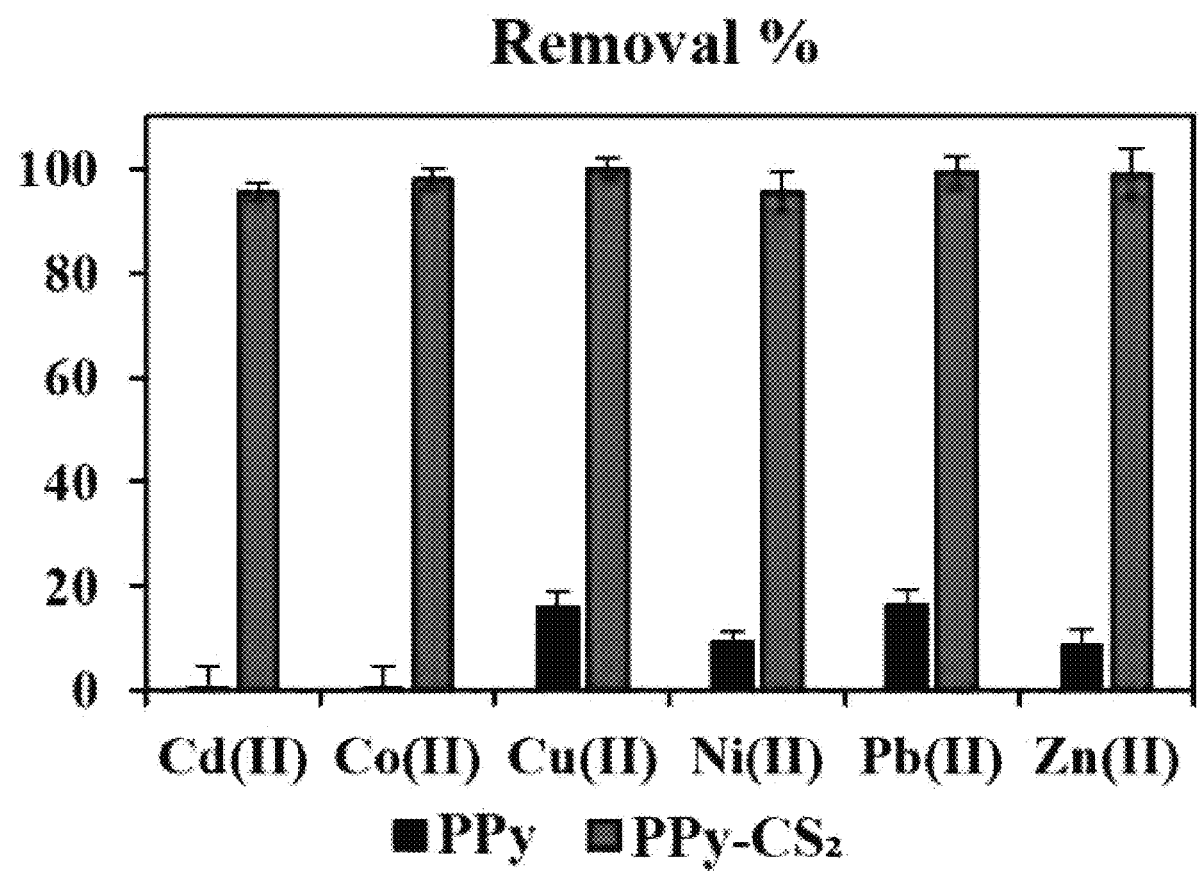
FIGS. 6A-6B: Comparative removal of the heavy metal ions by PPy and PPy-CS$_2$ from a multi-element solution containing 250 µg L$^{-1}$ of each metal ions (pH=5, sorption time=5 min) (FIG. 6A), and recovery of metal ions after desorption using 2 M nitric acid solution (FIG. 6B).
Figure 6B:
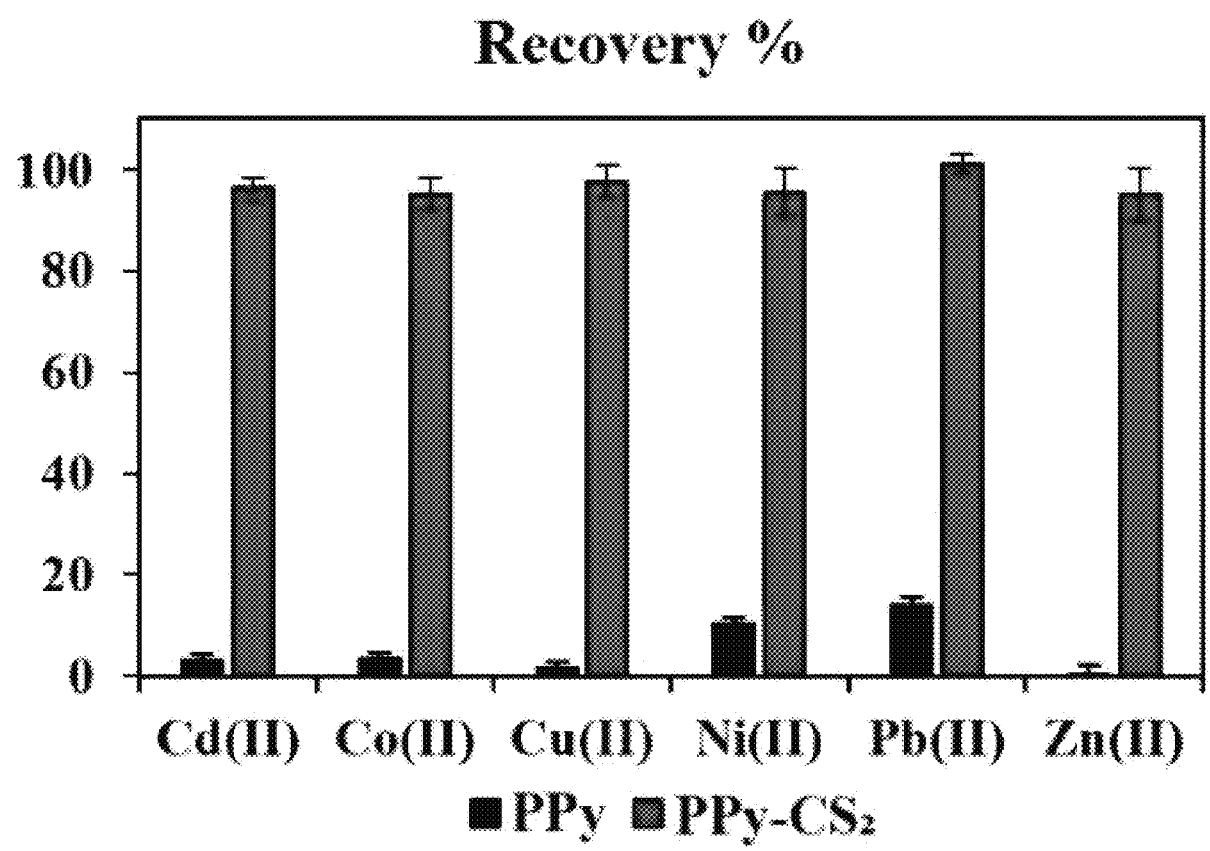

The efficiency of the PPy-$CS_2$ sorbent was compared to a PPy sorbent to investigate the effect of addition of the chelating group on the pyrrole-based polymer. The extraction of heavy metals was done in the same experimental conditions for PPy-$CS_2$ and PPy. The result shows that PPy can only extract the heavy metals with the efficiency of <17% in a short period of time, while PPy-$CS_2$ demonstrated >95% sorption efficiency in the same conditions (FIGS. 6A-6B).

UAD µ-SPE of Divalent Heavy Metal Ions

The air stability, chelating ability, and granular nature of the PPy-$CS_2$ polymer permit the insoluble polymer to be easily and homogeneously dispersed in aqueous solution for UAD µ-SPE of Cd, Co, Cu, Ni, Pb, and Zn. The extraction protocol was optimized by careful examination of the effect of pH of the extraction solution and the sorption and desorption time on the metal extraction and recovery.

Effect of pH

The pH of the working solution is an important variable for extraction of the metal ions in solid-phase extraction. In this case, the functional group of PPy-$CS_2$ polymer acts as the binding site for the metal and, thus, binding is affected by the protonation and deprotonation of the $CS_2$ functional group based on the pH of the solution. Metal binding and hence extraction is also affected by competing ions.

Figure 7:
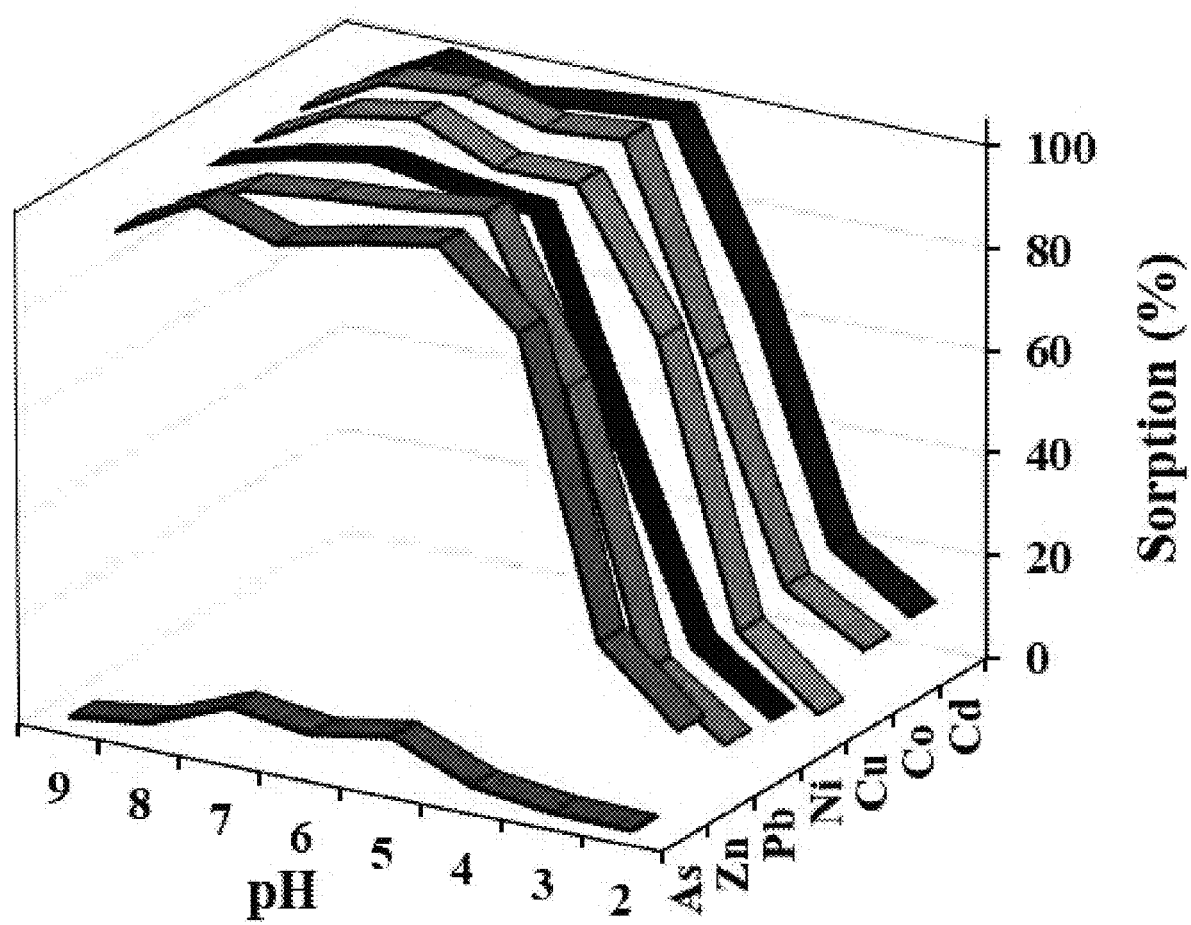
FIG. 7: Ultrasound assisted dispersive micro solid-phase extraction (UAD µ-SPE) of Cd(II), Co(II), Cu(II), Ni(II), Pb(II), Zn(II), and As(V) as a function of pH by PPy-CS$_2$.

In order to optimize the sorption condition, extraction conditions in the pH range of 2-9 were examined FIG. 7 shows the sorption efficiency increased rapidly in the pH range of 2.0-5.0 but changed little after that. In low pH, the dithioic (—$CS_2$) functional group of the polymer is protonated, which leads to less chelating capacity of the polymer. However, at the higher pH the dithioic acid group is deprotonated which leads to a negative charge generated on PPy-$CS_2$ chelating sites, which can result in greater attraction between the sorbent surface and the metal ions as well as more efficient complexation. Consistent with the colorimetric measurements, extraction of As (V), a hard ion, does not occur to any appreciable extent and further demonstrates the selectivity of PPy-$CS_2$. To avoid interference from metal hydroxides, a pH of 5.0 was used for further experiments.

Effect of Sorption Time and Desorption Flow Rate

Figure 8A:
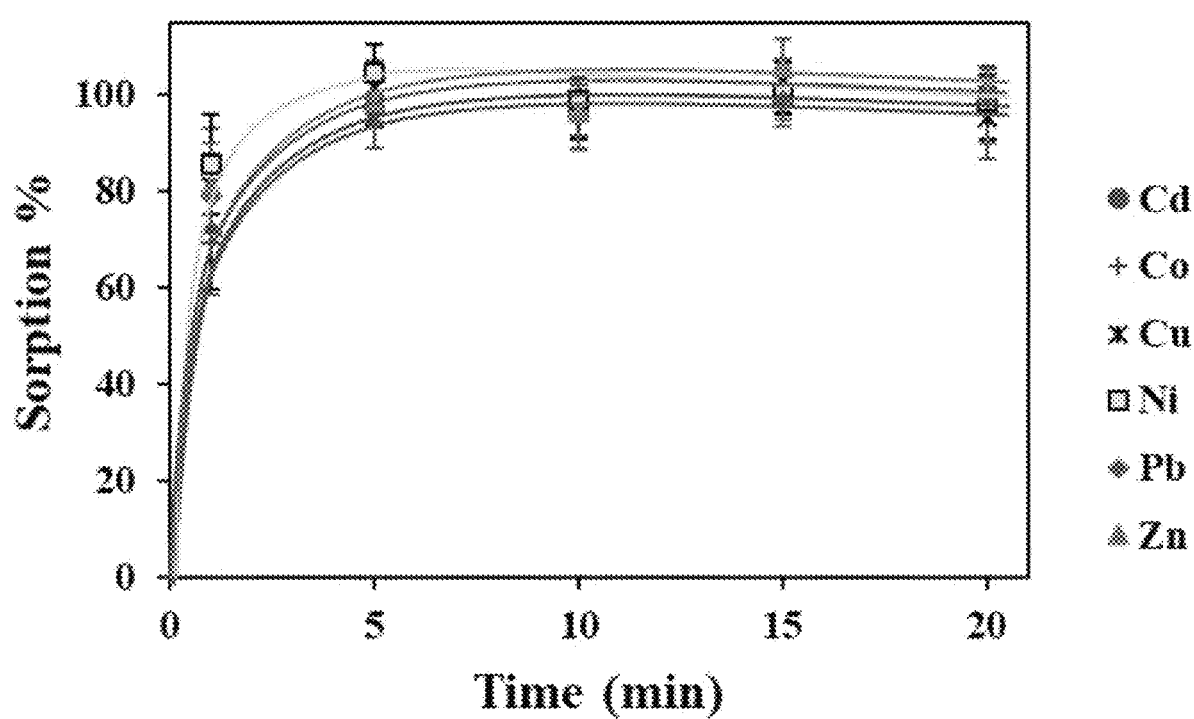
FIGS. 8A-8B: Sorption-time profiles for the PPy-CS$_2$ sorbent (FIG. 8A), and desorption-flow rate profiles for the PPy-CS$_2$ sorbent (FIG. 8B).

Sorption-time profiles were obtained by using solutions containing the six metal ions at concentrations of 250 µg $L^{-1}$ at pH 5 and for five different times of extraction. The excellent complexing strength of PPy-$CS_2$ along with other features of the polymer such as large surface area, electrostatic interaction of the negative charge of $CS_2$, and very good ultrasound-assisted dispersibility in water, resulted in obtaining excellent complexation kinetics. Therefore, the sorption of heavy metal ions on the polymer was very fast. Quantitative sorption was achieved very fast, in 1 min, as is demonstrated in FIG. 8A. The amount of metal extracted increased to a maximum at 5 min and then remained constant until 20 min. Therefore, 5 min was selected as the optimum sorption time needed to reach the equilibrium state.

Figure 8B:
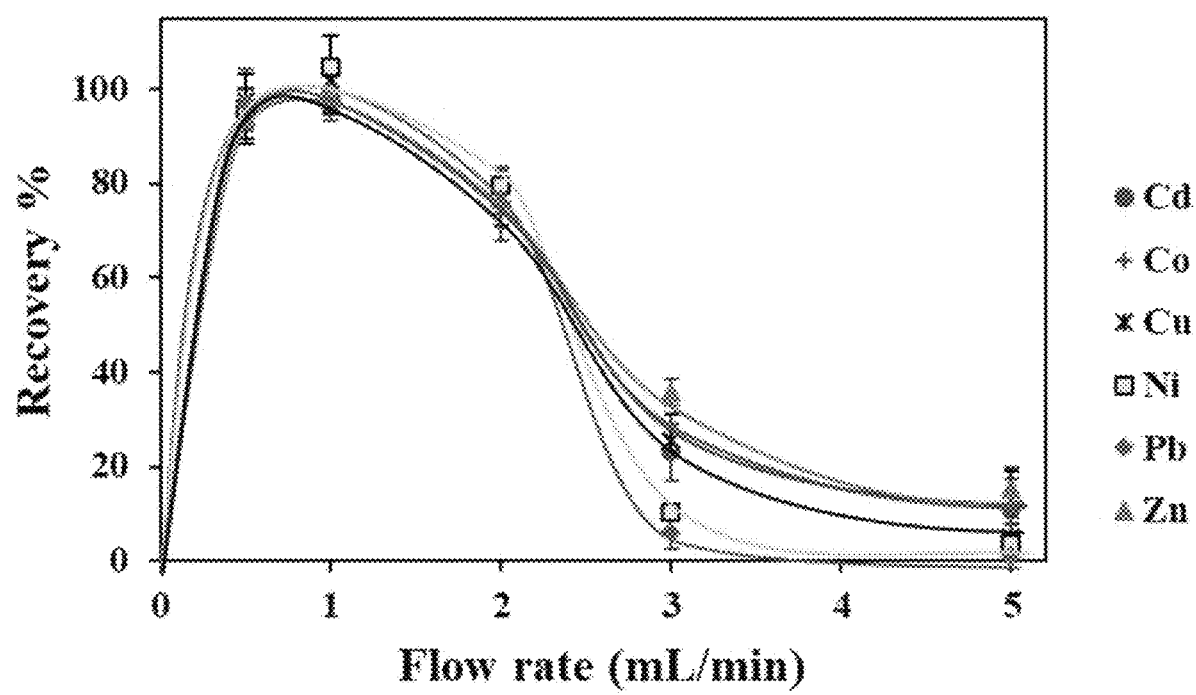

The effect of the eluent flow rate on the recovery of the metal ions from sorbent was also examined in the flow rate range of 0.5-5.0 mL min in the solutions containing the six metal ions at the concentrations of 250 µg $L^{-1}$ at pH 5. The total desorption volume was held constant at 1 mL. FIG. 8B shows that the quantitative recovery obtained is in the range of 0.5-1.0 mL min After that, the recoveries decreased because the contact time between retained metal ions and desorption solution was not sufficient for an effective elution. Based on the results, 1.0 mL min was selected as optimum elution flow rate for the rest of the experiments.

Metal Ion Extraction Efficiency by UAD µ-SPE

Under the optimized experimental conditions, the efficiency of the PPy-$CS_2$ sorbent to extract metal ions was compared to a PPy sorbent to investigate the effect of the incorporation of the $CS_2$ chelating group on the pyrrole-based polymer. Qualitatively, the EDX spectrum (FIG. 4C) of the polymer after extraction of heavy metals show peaks of all the corresponding metals, thus, confirming extraction of the metal ions.

To extract heavy metals (scheme 2, FIG. 2), 5 mg of the polymer was dispersed by ultrasound in a 10 mL aqueous solution containing 250 µg/L each of 6 metals (Co, Ni, Cu, Zn, Cd, and Pb). The technique of ultrasound assisted dispersive micro solid-phase extraction (UAD µ-SPE) allowed for enhanced extraction efficiency and reduced sorption time for the metals. The mixture was left for 5 minutes to allow for extraction of the metal ions by the dispersed polymer. The solution was then filtered with a 0.2 µm syringe filter, effectively trapping the particles in the filter. The filtrate was saved for ICP-MS analysis to determine the percent extraction (removal from the solution). The collected polymer was then washed with deionized water and followed by 2 M $HNO_3$ to desorb the metal ions from the trapped polymer. The desorption solution was then analyzed by ICP-MS to determine the percent recovery, which should be identical to the percent removal.

The results for metal ion removal and recovery are summarized in FIGS. 6A-6B. PPy is observed to extract the six metals with efficiencies of less than 17%. In contrast, all six metals were extracted with PPy-$CS_2$ with efficiencies of greater than 95%. Clearly, the inclusion of $CS_2$ as a chelating functional group dramatically improves the polymer extraction efficiency. Furthermore, the desorption process is essentially quantitative and regenerates the polymer for continued use, making PPy-$CS_2$ a useful material for quantitative analysis of metal ions.

FIG. 6A summarizes the results of the extraction and recovery experiments for poly(1H-pyrrole-1-carbodithioic acid) in this example. As can be seen, the recovery and extraction are essentially identical within experimental error and greater than 94% in each case, showing the excellent extraction and preconcentration properties of the pyrrole polymer 1H-pyrrole-1-carbodithioic acid. FIG. 6B summarizes the control experimental using polypyrrole prepared by an identical method and subjected to the same metal analysis procedure. It is important to note the dramatic reduction in the percent recovery and percent removal of the same metal ions. As seen from FIGS. 6A-6B, the functionalized pyrrole-based sorbent polymer shows high extraction efficiency for heavy metals as well as excellent recoveries. A lower efficiency compared to functionalized polypyrrole was observed.

Excellent recoveries for each metal were obtained ranging from 96.0 to 107.9%.

Evaluation of the Figures of Merit for Metal Ion Extraction and Analysis of a Certified Reference Standard Under the optimum experimental conditions, the UAD μ-SPE method with ICP-MS analysis was validated by evaluating the figures of merit. Limit of detections (LODs) were calculated using the equation LOD=$3S_d$/m, where $S_d$ is the standard deviation of the blank and m is the slope of the calibration curve. The LODs ranged from 0.3 ng $L^{-1}$ for Cd to 11.2 ng $L^{-1}$ for Zn with linear ranges between 0.1-500 μg $L^{-1}$. Limits of quantification (LOQ) were determined according to the equation LOQ=$10S_d$/m to be in the range of 1.0-37.5 ng $L^{-1}$. All of the analytical figures of merits are summarized in Table 1. Table 2 summarizes provides valuable comparisons. UAD μ-SPE using the PPy-CS$_2$ polymeric sorbent material performs as well or better than known analytical methods using different extraction approaches.

TABLE 1

Analytical Figures of Merits

| Parameter | Cd | Co | Cu | Ni | Pb | Zn |
|---|---|---|---|---|---|---|
| LDR[a] | 0.1-500 | 0.1-500 | 0.1-500 | 0.1-500 | 0.1-500 | 0.1-500 |
| $R^2$ | 0.997 | 0.998 | 0.998 | 0.999 | 0.997 | 0.998 |
| LOD[b] | 0.3 | 0.4 | 6.3 | 2.1 | 0.6 | 11.2 |
| LOQ[c] | 1.0 | 1.2 | 21.1 | 7.0 | 2.0 | 37.5 |
| RSD[d] | 3.5 | 3.6 | 3.4 | 4.9 | 2.2 | 6.3 |

[a]Linear dynamic range (μg $L^{-1}$).
[b]Limit of detection (ng $L^{-1}$).
[c]Limit of quantification (ng $L^{-1}$).
[d]Relative standard deviation (%), n = 5.

TABLE 2

Comparison of Various Extraction Methods for Metal Ion Determination

| Metal ion | Extraction Step [Method] | LDR[a] | LOD[b] | RSD (%)[c] | Detection |
|---|---|---|---|---|---|
| Cd, Co, Cu, Ni, Pb, Zn | UAD-μSPE | 0.1-500 | 0.0003-0.00112 | 2.2-6.3 | ICP-MS |
| Cd, Cr, Mn, Fe, Pb, Zn | DMSPE[1] | 0.5-1000 | 0.06-0.25 | 1.6-3.0 | ICP-OES |
| Cd, Co, Cu, Ni, Pb, Zn | ABS[2] | 4-400 | 0.06-4.9 | 0.9-4.0 | MP-AES |
| Bi, Hg, Pb | Chip-Based Array Monolithic Microextraction | 0.05-20 | 0.0012-0.0023 | 2.3-3.7 | ICP-MS |
| Cd, Co, Cu, Cr, Ni, Mn, Pb | MSPE[3] | 2.5-250 | 0.2-0.9 | 2.9-6.6 | ICP-OES |

[a]Linear dynamic range (μg $L^{-1}$).
[b]Limit of detection (μg $L^{-1}$).
[c]Relative standard deviation.
[1]Dispersive micro solid phase extraction.
[2]Aqueous biphasic system microextraction.
[3]Magnetic solid-phase extraction Certified reference standard CRM-TMDW was analyzed to provide a measure of reliability of the method for accurately determining metal ion concentrations. Table 3 summarizes the results for the analysis of the six metal ions in CRM-TMDW. Excellent recoveries for each metal were obtained ranging from 96.0 to 107.9%. It is important to note the CRM-TMDW drinking water standard contained twenty-nine trace metals including high levels of Na (6000 μg $L^{-1}$), K (2500 μg $L^{-1}$), Ca (35,000 μg $L^{-1}$), Mg (9000 μg $L^{-1}$), and Fe (100 μg $L^{-1}$). The high recovery values obtained in this complex solution of ions clearly demonstrated the excellent selectivity afforded by this method.

TABLE 3

Analysis of Certified Reference Material CRM-TMDW with UAD μ-SPE and the PPy-CS$_2$ Polymer

| CRM | Metal Ions | Certified concentration (μg $L^{-1}$)[b] | Determined concentration (μg $L^{-1}$)[c] | Recovery (%) |
|---|---|---|---|---|
| CRM-TMDW[a] | Cd | 10.0 ± 0.2 | 10.8 ± 0.9 | 107.9 |
| | Co | 25.0 ± 0.4 | 24.7 ± 0.6 | 98.8 |
| | Cu | 20.0 ± 0.3 | 21.4 ± 1.1 | 106.9 |
| | Ni | 60.0 ± 0.9 | 61.8 ± 1.2 | 103.0 |
| | Pb | 40.0 ± 0.8 | 38.4 ± 2.2 | 96.0 |
| | Zn | 70.0 ± 1.1 | 71.4 ± 1.1 | 102.0 |

[a]Certified reference material of trace metals in drinking water.
[b]The uncertainty in the certified value is calculated for a 95% confidence interval and coverage factor of about 2.
[c]The reported uncertainty is related to one standard deviation (Mean ± SD, n = 4).

Conclusion

An N-functionalized derivative of pyrrole was synthesized and chemically polymerized to generate the polymeric sorbent material PPy-CS$_2$ for trace determination of heavy metal ions. PPy-CS$_2$ is useful as a polymeric sorbent material for ultra-trace determination of heavy metal ions. Existing polypyrrole-based composites used for heavy metal extraction lack an effective chelating moiety and are mostly based on weak and unselective interactions. PPy-CS$_2$ was found to be an air stable, granular material that is easily manipulated as a sorbent material or dispersed in solution for UAD μ-SPE. The bidentate carbodithioate moiety readily chelates divalent heavy metals, including Cd(II), Co(II), Cu(II), Ni(II), Pb(II), and Zn(II), in a selective and reversible manner such that it can be used as an effective sorbent for quantitative analysis of heavy metals by ICP-MS. The reversible chelation and desorption of specific heavy metals is a clear advantage of PPy-CS$_2$ as a sorbent material over PPy, which interacts with metals by weak and unselective interactions. The metal specific sorption mechanism of PPy-$CS_2$ along with its dispersibility provided for the development of an environmentally friendly UAD μ-SPE method to achieve fast, simple, and accurate determination of heavy metals in aqueous media with minimal sample volume and the absence of organic reagents.

The interesting sorption properties of PPy-$CS_2$ along with its dispersibility properties allowed for its use in the UAD μ-SPE technique to achieve a fast, simple, and effective determination of heavy metals in water samples. Thus, these examples demonstrate that poly(1H-pyrrole-1-carbodithioic acid) (PPy-$CS_2$) is a highly efficient sorbent material for the extraction of heavy metal ions. The polymer is also easily handled and can therefore be utilized in a number of applications.

Example II—Pyrrole-Based Conductive Polymer for Extraction, Recovery, and Quantitative Determination of Rare Earth Elements The International Union of Applied and Pure Chemistry (IUPAC) defines rare earth elements (REEs) as a group of 15 lanthanides in addition to scandium (Sc) and yttrium (Y) that are naturally found in the environment. Due to their unique optical, electrical, and magnetic properties, REEs are widely used in permanent magnets, batteries, high tech fields. and the defense industry. Currently, the global production of REEs is about 130,000 metric tons of rare earth oxide (REO) per year worth approximately US $2.05 billion. The increase in usage of REEs has led to an increase in demand, especially within China which consumed 119,000 tons of REO in 2014. The largest part of the demand is still fulfilled by non-renewable primary sources such as mines. A further drawback of mine production is that lanthanum (La) and cerium (Ce) are currently the most abundant elements, while the demand for other scarcer lanthanides such as neodymium (Nd) or Dysprosium (Dy) is increasing. These challenges can be addressed by new recovery approaches for REEs, such as extraction and removal of REEs from secondary resources such as acid mine drainage, low grade REE industrial residues, and mine tailings. Furthermore, the production of REEs from primary resources is a time consuming, multi-step process with generation of large amounts of toxic waste during the process.

Due to the demand for REEs for many important applications, efficient, green, low cost, and selective extraction techniques are needed to recover REEs. Several techniques have been used to determine REEs including ultraviolet-visible spectroscopy (UV-vis), chemiluminescence, molecular fluorescence, and potentiometry. However, the concentrations of REEs exist at much lower concentrations than the detection limits (LOD) of most of these approaches. Various methods such as reduction-extraction chromatography, resin based extraction, and liquid-liquid extraction have been used for extraction of REEs. Different polymeric materials have been used for extraction of REEs, but these techniques often require large amounts of organic solvents, are time consuming, and lack the needed selectivity to extract metals from complicated matrices.

Polypyrrole (PPy) is a conductive polymeric adsorbent that has been used for extraction of several organic and inorganic analytes. PPy is a cost-effective and porous material with excellent chemical and thermal stability, and no reported solubility in water. These features make PPy-based materials good candidates for extraction of a variety of materials. Sorbent materials based on polymeric and nano-composites of pyrrole and thiophene have been successfully developed and utilized for microextraction of polar analytes, the hepatotoxins microcystin, and heavy metals. In this example, a green synthesis procedure is used in which pyrrole is functionalized with carbon dioxide to produce 1H-pyrrole-1-carboxylic acid (Py-$CO_2$), (Scheme 3, FIG. 12). The Py-$CO_2$ was chemically polymerized to obtain an air stable, granular, black polymeric powder, poly(1H-pyrrole-1-carboxylic acid) (PPy-$CO_2$). This polymeric material was utilized for the extraction, recovery, and quantitative determination of REEs and other metals including heavy metals by ultra sound assisted dispersive micro solid-phase extraction (UAD μ-SPE).

Reagents and Solutions

All chemicals were of analytical grade and used as received. Water from a Barnstead B-pure water purification system (>17 MΩ cm) was used for preparation of all aqueous solutions. The pH was adjusted with dilute nitric acid and sodium hydroxide. ICP-MS standard solution of 71 elements in nitric acid matrix was purchased from Inorganic Ventures (Christiansburg, Va.). Potassium tert-butoxide was purchased from Millipore Sigma (St. Louis, Mo.). Ferric chloride ($FeCl_3$) and ammonium persulfate (APS) were purchased from Fisher Scientific and used as oxidizing agents. Pyrrole was purchased from Sigma Aldrich (Milwaukee, Wis.) and was distilled before each use. Hydrophilic-based PTFE membrane syringe filters purchased from Fisher Scientific (Pittsburgh, Pa.) were used for sample filtration.

Instrumentation

All samples were analyzed for metal ions using a Thermo Scientific XSeries 2 inductively coupled plasma mass spectrometer (San Jose, Calif.) equipped with a slurry nebulizer. A Perkin-Elmer Frontier Fourier transform infrared (FTIR) spectrometer (Shelton, Conn.) was used in the attenuated total reflectance (ATR) mode. Measurements of pH were done using a Basic pH Meter (Denver Instrument Company, Denver, Colo.). A JEOL JSM-7500F scanning electron microscope (JEOL USA, Inc., Peabody, Mass.) equipped with a BRUKER XFlash 5010 series energy dispersive X-ray spectroscopy (EDX) detector (Billerica, Mass.) was used to obtain scanning electron microscopy (SEM) images and EDX spectra. Thermogravimetric analysis was performed on TA Instruments SDT 2960 simultaneous TGA-DTA (New Castle, Del.). NMR spectra were acquired using an Avance III 600 MHz spectrometer. Mass spectra were acquired on a Synapt High Definition Mass Spectrometer (HR-MS) (Milford, Mass.).

Synthesis of PPy-$CO_2$

Figure 13:
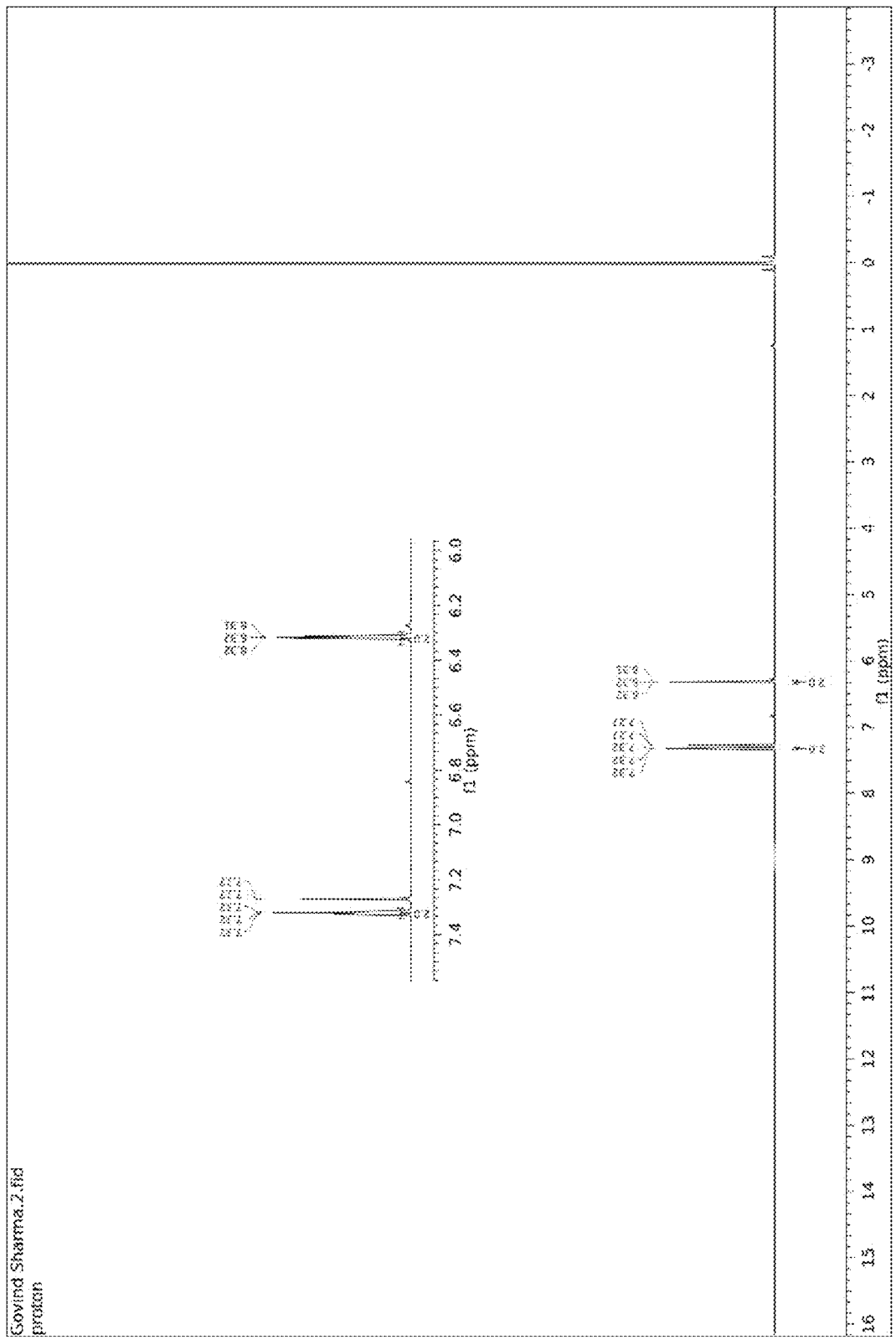
FIG. 13: $^1$H NMR spectrum of 1H-pyrrole-1-carboxylic acid.
Figure 14:
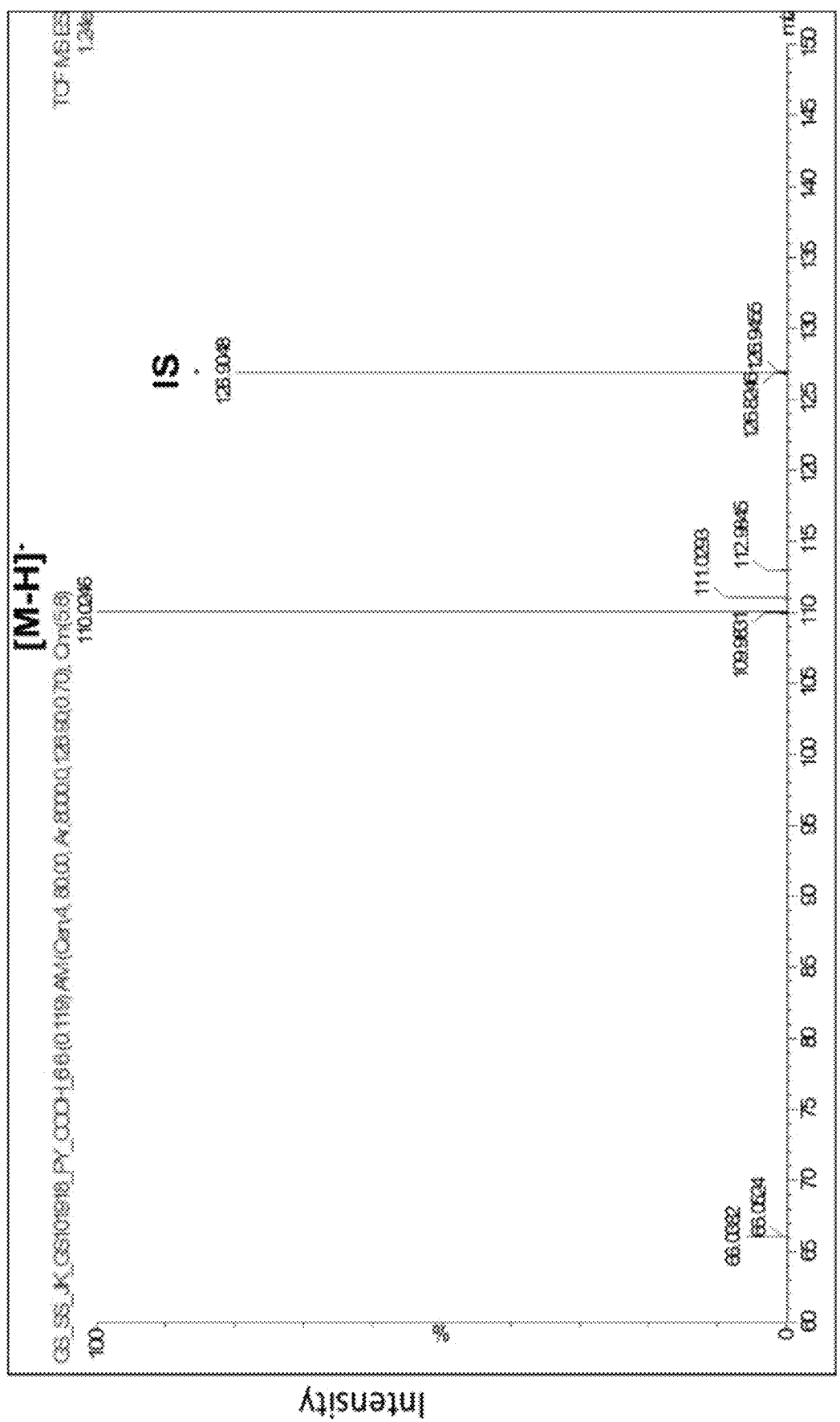
FIG. 14: HRMS data for 1H-pyrrole-1-carboxylic acid.

The synthetic route for 1H-pyrrole-1-carboxylic acid is depicted in FIG. 12 (Scheme 3). Firstly, a 0.5 M solution of diethyl ether:THF (1:1) was prepared. To this solution, a strong base such as potassium tert-butoxide was added and cooled below room temperature. To this mixture, pyrrole was added dropwise, and the reaction mixture was warmed to 25° C. followed by addition of excess solid $CO_2$. The reaction was allowed to continue until no $CO_2$ remained $H_2O$ (100 mL) was then added and the reaction mixture was transferred to a separatory funnel. The aqueous layer was collected, and the organic phase was washed with 100 mL of water. To the collected aqueous layers, 1 M aqueous hydrochloric acid was added dropwise to acidify the solution. To this solution, 100 mL of diethyl ether was added and again transferred to a separatory funnel. The organic phase was collected, and the aqueous layer was extracted with diethyl ether (3×50 mL) to remove the unreacted pyrrole. The combined organic extracts were dried over anhydrous sodium sulfate, filtered, and concentrated to obtain pure product (3), which was used for NMR, HRMS, and FTIR characterization. (FIG. 13.) $^1$H NMR (600 MHz, CDCl$_3$): δ (ppm) 7.30 (t, 2H, J=2 Hz), 6.30 (t, 2H, J=2 Hz); HRMS-ESI m/z calculated for C$_5$H$_4$NO$_2$ [M-H]$^-$: 110.0242, found 110.0246 (FIG. 14).

Poly(1H-pyrrole-1-carboxylic acid) (PPy-CO$_2$) was synthesized using a chemical polymerization method with APS as the oxidizing agent. Once the monomer was synthesized, 0.55 mg (0.02 mol) of Py-CO$_2$ was placed in a round bottom flask. Then, 9.13 g of APS (0.04 mol) in 20 mL deionized water was added at a rate of 10 mL h using a syringe pump. The reaction mixture was stirred overnight at room temperature to complete the polymerization. Next, with the aid of vacuum filtration, the polymer was separated from excess reagents and solvents. The filtrate was washed several times with 1 M HCl solution, ethanol, and deionized water. A dark black powder of PPy-CO$_2$ (4) was air dried and stored at room temperature.

Figure 15:
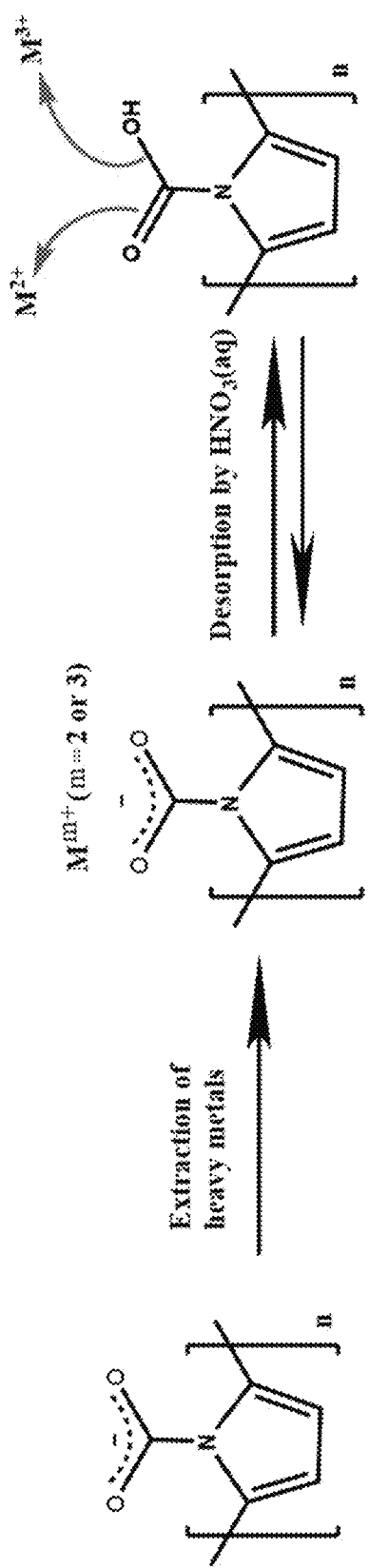
FIG. 15: Scheme 4, showing the mechanism of the extraction and desorption of metal ions by PPy-CO$_2$.

Extraction Procedure 10 mg of PPy-CO$_2$ was first dispersed in a 10 mL aqueous solution containing 250 μg L of each metal ion using an ultrasonic bath to aid dispersion. The stable dispersed mixture was left for 30 min to complete the sorption of metals ions to the polymer. Then, the dispersed solution was carefully transferred to a 12 mL syringe and filtered using a 0.2 μm syringe filter (PTFE membrane, pore size 0.2 μm). The remaining solution was saved for inductive coupled mass spectrometry (ICP-MS) analysis to determine the % removal. The filtered polymer was sequentially washed with deionized water and 1 mL of 2 M nitric acid solution to perform the metal desorption step. The eluted solution was also used for ICP-MS analysis to obtain the % recovery of the UAD μ-SPE procedure. Scheme 4 (FIG. 15) shows the extraction and desorption procedure for divalent and trivalent metal cations with PPy-CO$_2$.

Results and Discussion

The PPy-CO$_2$ polymer is useful for extraction of metal ions from aqueous solution, especially hard metal ions. Incorporation of the CO$_2$ functional group permits bidentate chelation, thus enhancing the extraction efficiency and the ability to preconcentrate metals for analysis (Scheme 4, FIG. 15). Furthermore, the oxygen atom is a hard electron donor and provides a higher affinity towards trivalent metals, especially REEs, which are relatively hard cations. Additionally, the carboxylic acid group makes the polymer similar to the above-described PPy-CS$_2$ polymer due to its ability to reversibly protonate and deprotonate, permitting easy extraction and desorption of metals by a simply change in the solution pH. At neutral pH conditions, the carboxylic acid group can be deprotonated thereby promoting the electrostatic attraction between the negatively charged carboxylate anion and the positively charged metal cations, allowing for improved chelation and hence better extraction. Similarly, in acidic conditions, the carboxylate group can be protonated or neutral for metal desorption followed by analysis. As a result, metal chelation in PPy-CO$_2$ is reversible and can be reused for further extractions. Hence, this polymer offers the ability for the trace determination of a wide range of metal ions, including REEs. By utilizing the polymer as a sorbent material with an UAD μ-SPE method, efficient extraction and analysis of dissolved metal ions is possible.

Characterization of the PPy-CO$_2$ Sorbent Material

Figure 16A:
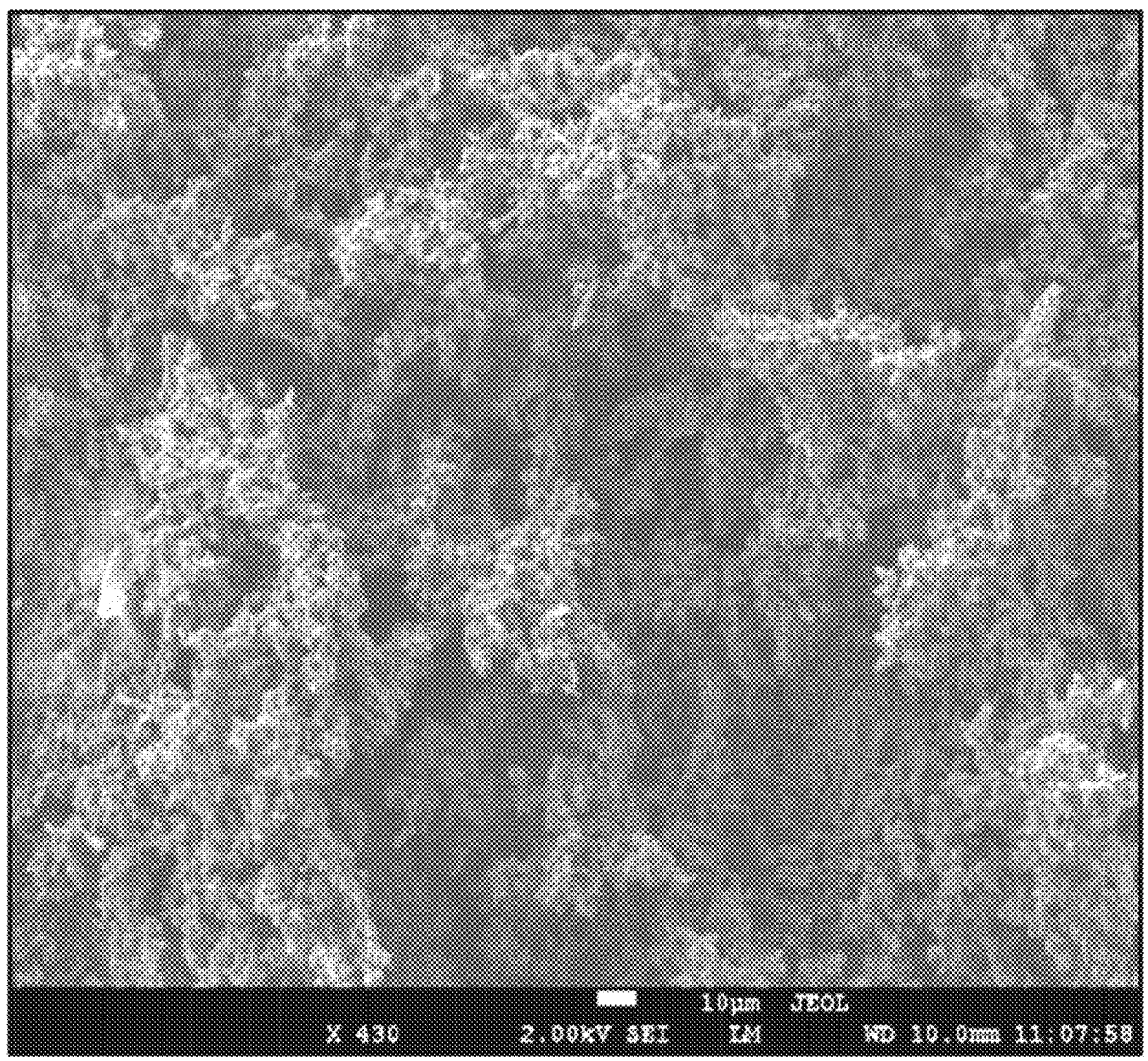
FIGS. 16A-16D: SEM image of the PPy-CO$_2$ polymer (low magnification (×430)) (FIG. 16A), high magnification for morphology of the polymer (FIG. 16B), high magnification for particle size estimation (×65000) (FIG. 16B, inlet), SEM-EDX spectrum of PPy (FIG. 16C), and SEM-EDX spectrum of PPy-CO₂ (FIG. 16D).
Figure 16B:
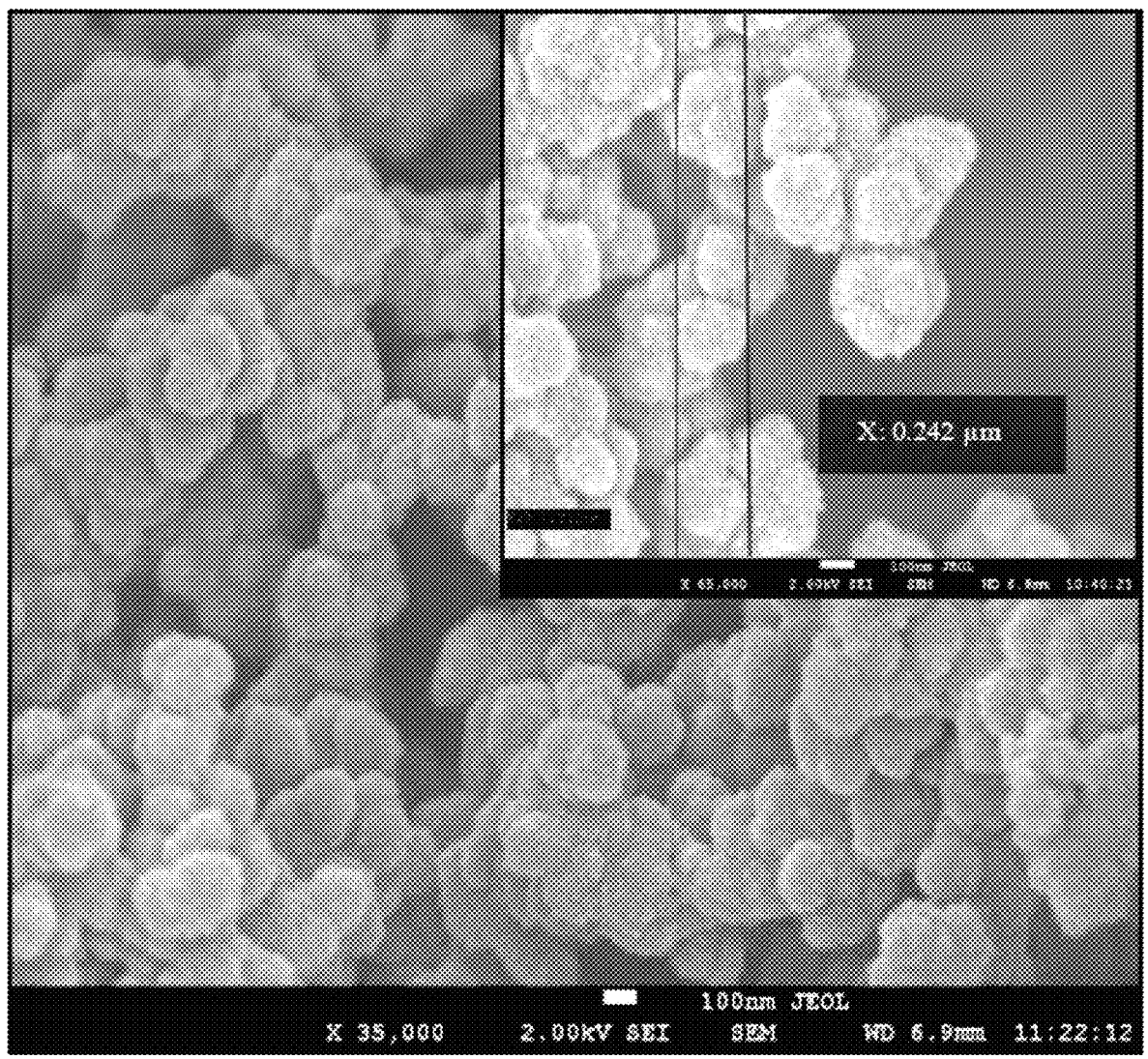
Figure 16C:
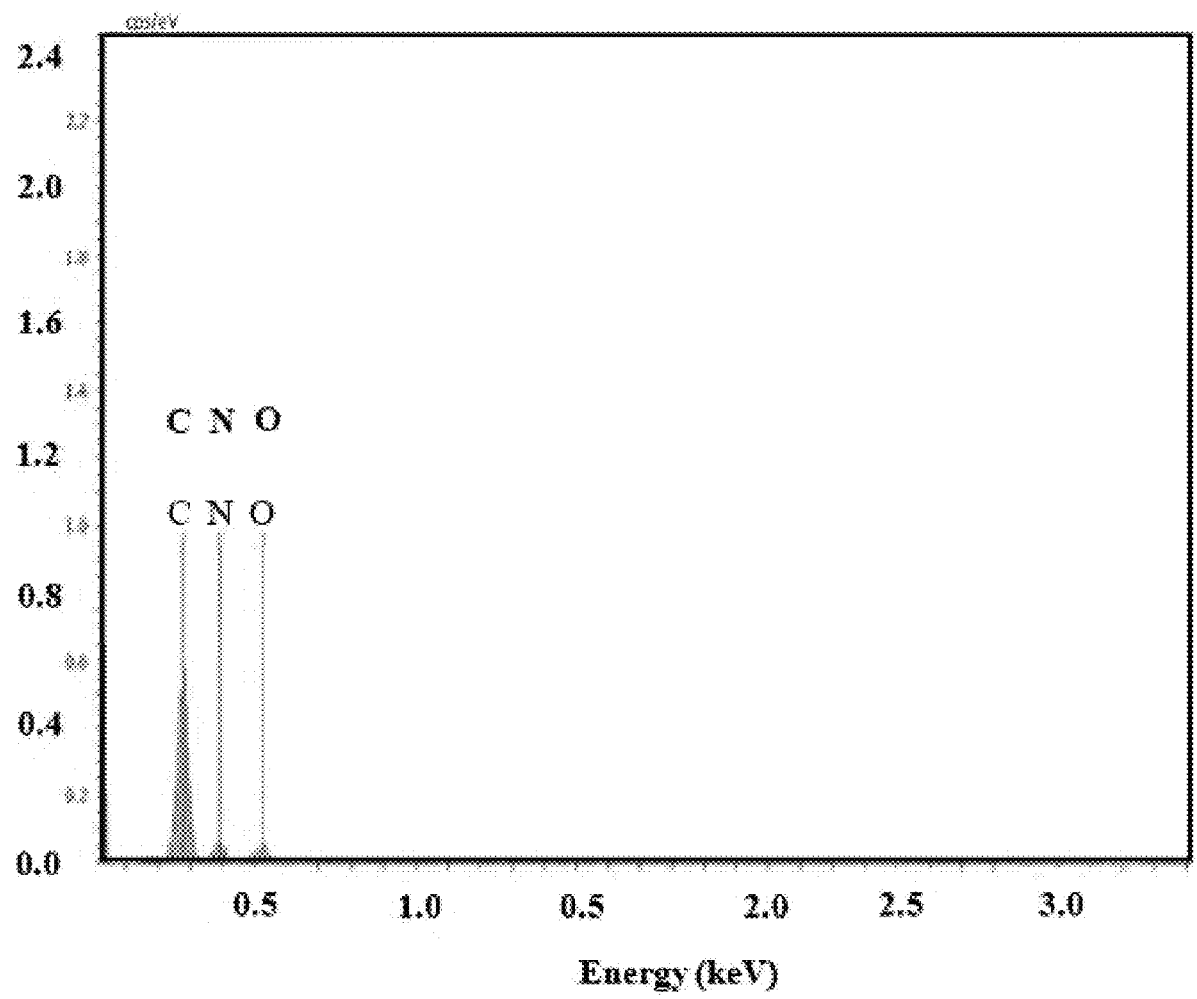
Figure 16D:
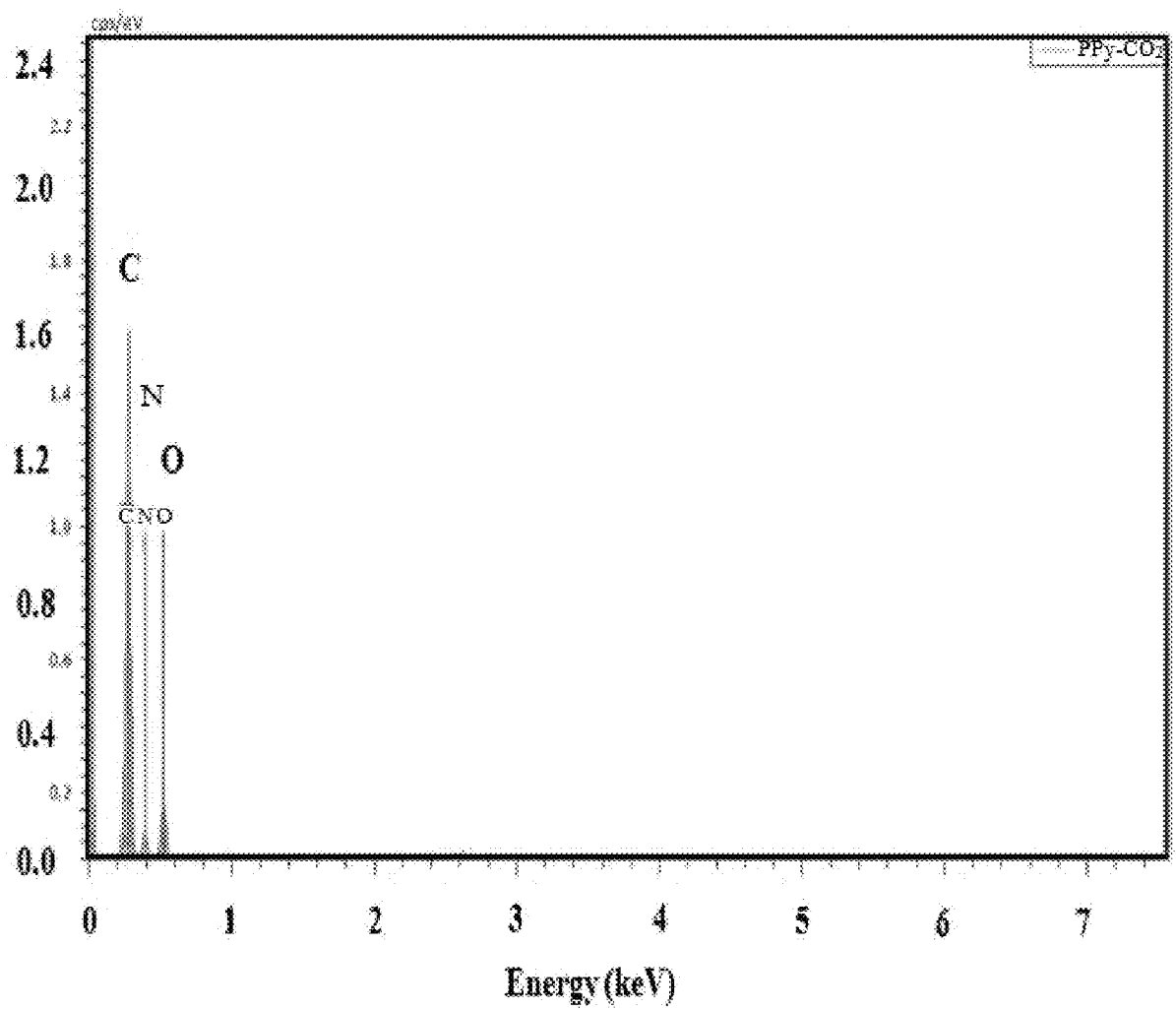

The functionalization of pyrrole with carboxylic acid readily produces the monomer 1H-pyrrole-1-carboxylic acid. After the chemical polymerization, PPy-CO$_2$ is created as a black, air stable dark powder. The SEM images for the PPy-CO$_2$ at different magnification are shown in FIGS. 16A-16B, representing the porous granular structure. The particle size was evaluated from FIG. 16B (inlet) and other SEM pictures, and was found to be approximately 0.23-0.32 μm. FIGS. 16C-16D represent the EDX spectra of PPy and PPy-CO$_2$, respectively. In comparison, both spectrums shows the presence of carbon and nitrogen. However, the intensity of oxygen in FIG. 16D is higher compared to FIG. 16C. The presence of oxygen in FIG. 16C may be because of adsorbed atmospheric oxygen or from the SEM sample holder which is made of Al$_2$O$_3$. This is further confirmed by FTIR analysis (FIGS. 17A-17B), which shows PPy has no oxygen-containing functional groups whereas a characteristic absorption band for carbonyl is observed in both the spectra of Py-CO$_2$ and PPy-CO$_2$.

Figure 17A:
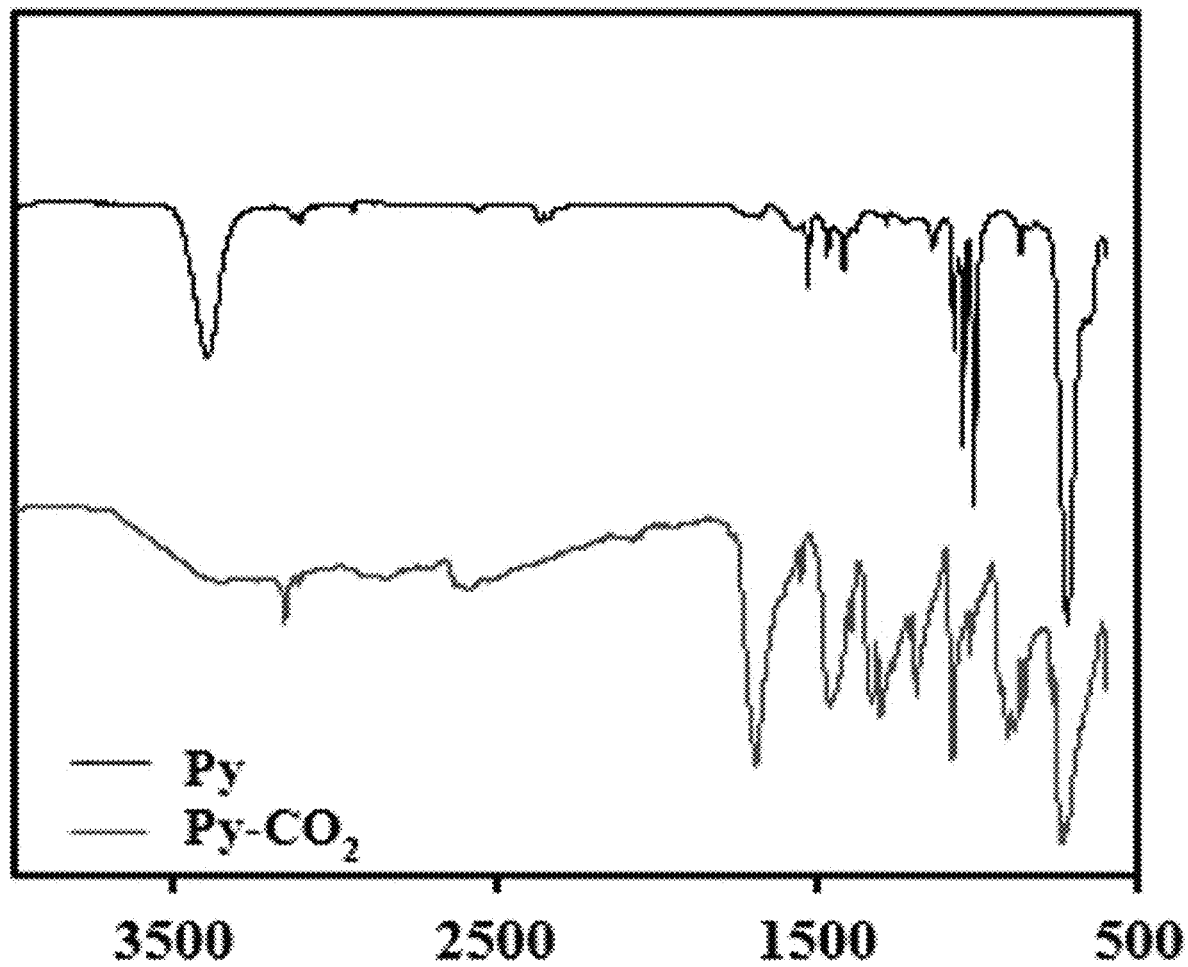
FIGS. 17A-17B: FTIR spectra of monomers (Py and Py-CO₂) (FIG. 17A), and the corresponding polymers (PPy and PPy-CO₂) (FIG. 17B).
Figure 17B:
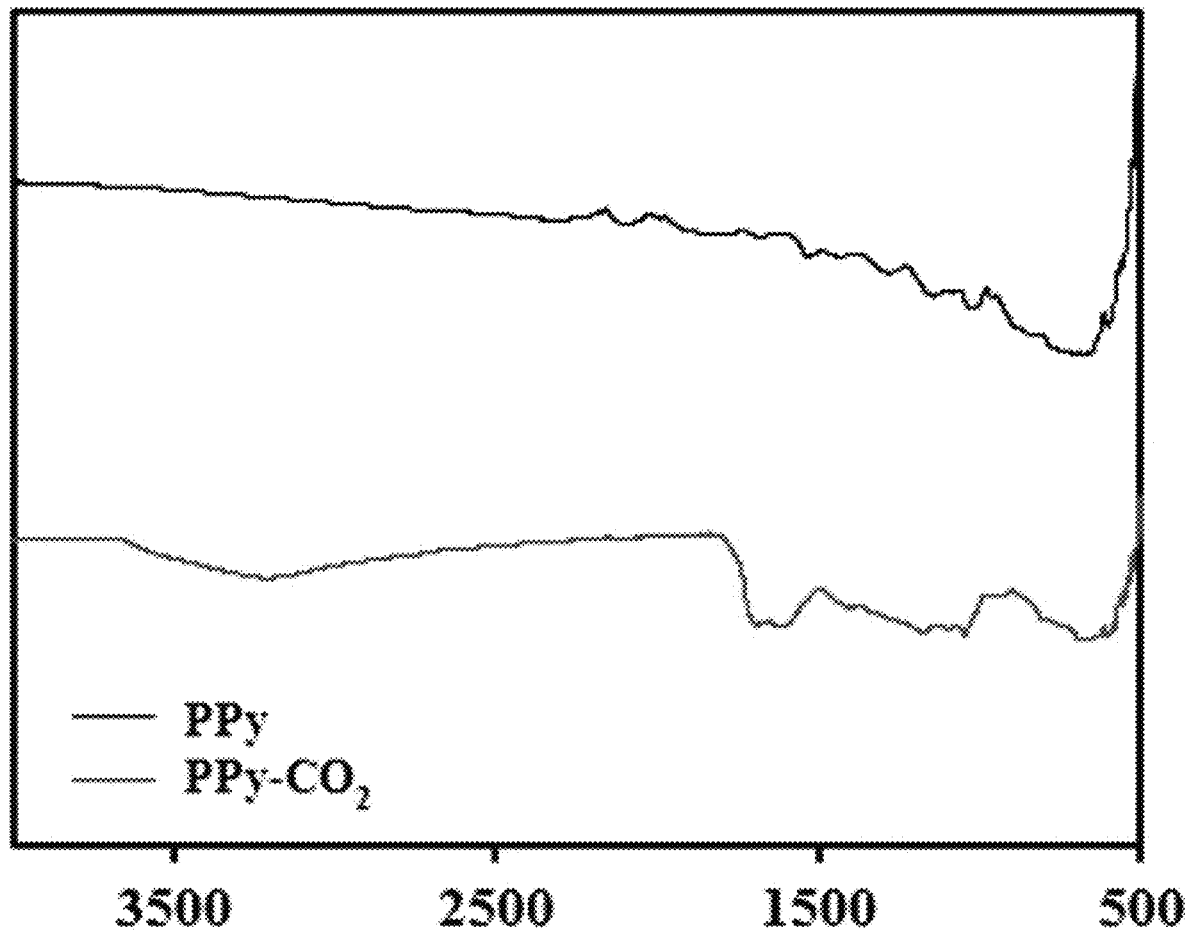
Figure 18:
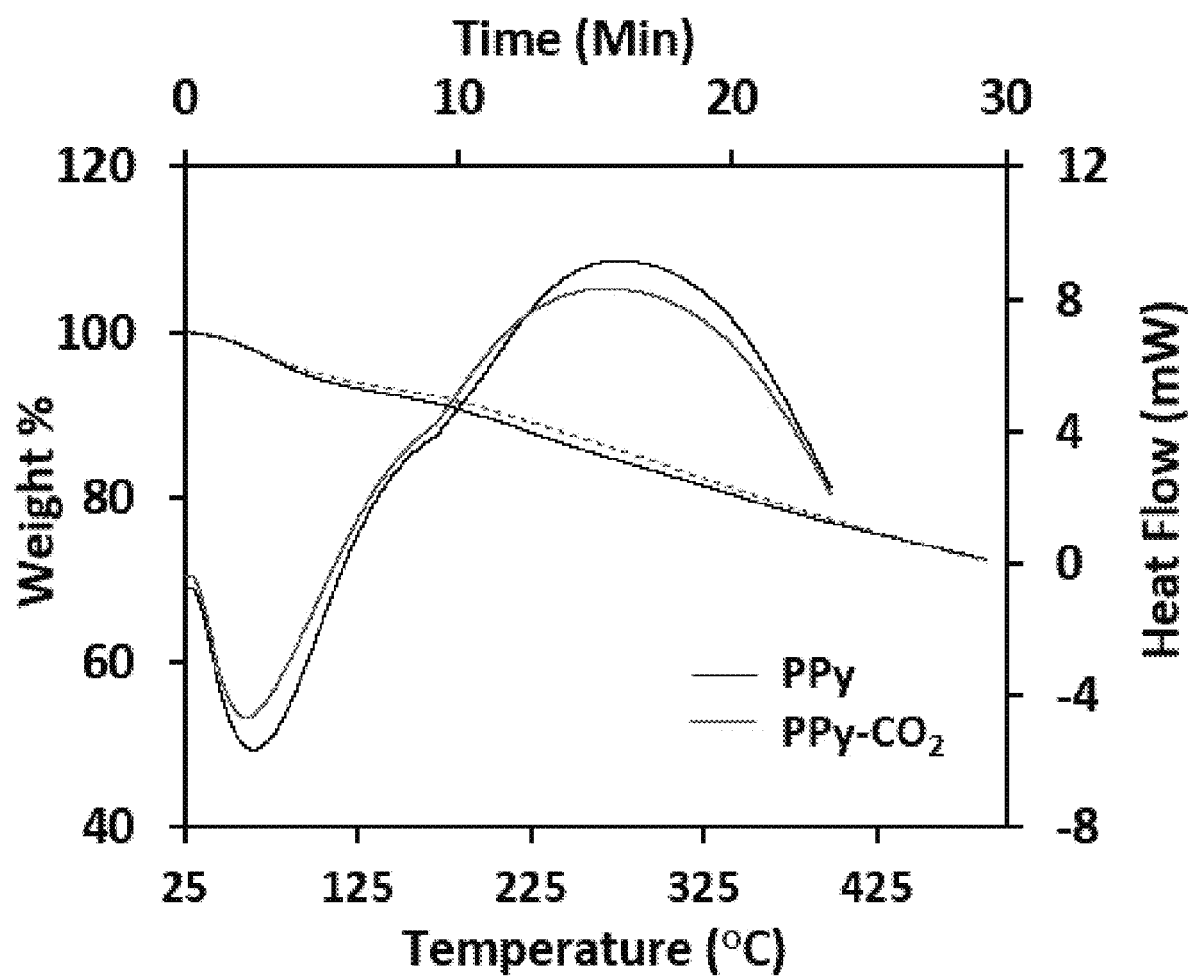
FIG. 18: TGA-DSC curves for PPy and PPy-CO₂.

The synthesized Py-CO$_2$ and PPy-CO$_2$ materials were also examined by FTIR and compared to unfunctionalized Py and PPy (FIGS. 17A-17B). In FIG. 17B, absorption bands characteristic to polypyrrole due to the presence of C=C stretching near 1550 cm$^{-1}$ and 1470 cm$^{-1}$, C—N peaks around 1300 cm$^{-1}$, and =C—H out of plane vibrations at 700 cm$^{-1}$ and 970 cm$^{-1}$ are also seen in PPy-CO$_2$. Additionally, the C=O characteristic band in PPy-CO$_2$ is seen near 1670 cm$^{-1}$, while C—O is observed near 1050 cm$^{-1}$ and the broad stretching feature due to the carboxylic acid O—H occurs at near 3000 cm$^{-1}$. Thermogravimetric analysis was also performed on the synthesized PPy-CO$_2$ polymer at 20° C./min under air (FIG. 18) and the data were compared with PPy. The synthesized PPy-CO$_2$ exhibited similar thermal behavior to PPy showing stability up to 400° C. losing only 20% of its weight, indicating that this polymer may be used in high temperature applications.

Extraction of REEs by UAD μ-SPE

The granular micro sphere-like nature, air and thermal stability, and chelating property of PPy-CO$_2$ allow the insoluble polymer to be effectively and uniformly dispersed in aqueous solution for UAD μ-SPE of REEs. Various experimental parameters were examined to obtain the conditions for maximum extraction, recovery, and determination of REEs. This included evaluating the effect of pH of the extraction and desorption solutions, the amount of polymer required, extraction time, and desorption flow rate.

Effect of Extraction Solution pH

The impact of extraction solution pH is a significant variable for effective extraction of REEs in solid phase extraction. In this example, the carboxylic acid functional group of PPy-CO$_2$ acts as a chelating site for the REEs and other metals and, consequently, the chelating ability is influenced by protonation and deprotonation of the CO$_2$ group. Thus, the process of chelation and extraction is influenced by competing ions. The effect of extraction solution pH on the sorption conditions was carefully studied in the pH range of 2.0 to 8.0 to evaluate extraction conditions. The sorption efficiency for different metal ions as a function of pH is shown in FIGS. 19A-19B. FIGS. 19A-19B show the broad range applicability of PPy-CO$_2$ for the extraction of REEs along with important metals including toxic heavy metals. FIGS. 19A-19B demonstrate that the sorption efficiency for Be, Cr, Fe, Cu, Zn, Ag, REEs, Au, Pb, and Th increases with the increase in pH from 2.0 to 6.0. Further increase in pH from 6.0 to 7.0 resulted in decreased extraction efficiency. In contrast, the maximum sorption for Mg, Mn, Co, Ni, As, Se, Rb, Cs, and Ba was observed at pH 8.0. These results indicate that the CO$_2$ functional group on the polymeric backbone is protonated at low pH conditions, diminishing the chelating ability of the polymer, whereas at high pH values, the $CO_2$ group is deprotonated, leading to negatively charged $CO_2$ and creating active binding sites for chelation of metal ions. Increasing the pH from 7.0 to 8.0 can lead to the formation of hydroxides of metals. Therefore, caution may be taken to avoid adsorption on the polymeric material during the filtration process. Consequently, higher pH values were avoided, and pH 6.0 was used as an optimum extraction solution pH.

An important advantage of the $PPy-CO_2$ polymeric material as a sorbent is the ability to extract a wide range of metals ranging from +2 cations to +3 cations. The hard electron donating carboxylic acid group accounts for the expansion of the number and types of metals that can be extracted. $PPy-CO_2$ is unique in its ability to extract and recover the hard +3 REE metal cations at greater than 95% efficiency.

Optimization of Amount of $PPy-CO_2$

The amount of polymer utilization for maximum extraction of targeted metal ions from a multi element solution containing 250 μg $L^{-1}$ of each metal ions was evaluated. FIGS. 20A-20B show the plot of percent removal of various metals as a function of the amount of sorbent material ranging from 1-25 mg. The removal efficiency of the sorbent material for REEs increased from 1 to 10 mg of polymer until plateauing (FIG. 20B). Incorporation of more sorbent above 25 mg lead to no obvious improvement in extraction efficiency for +3 cations and REEs. However, the extraction efficiency for other metal ions did show a slight increase, which may be due to adsorption or chelation (FIG. 20A). Hence, 10 mg of polymer was chosen as the optimum amount.

Certain embodiments of the compositions and methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A composition comprising Formula A:

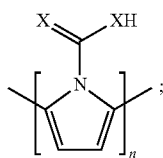

Formula A wherein:
each X is independently either S or O, provided that at least one X is O, and
n is an integer greater than 1;
and salts, stereoisomers, racemates, hydrates, solvates, polymorphs, and complexes thereof.

2. The composition of claim 1, wherein n ranges from 2 to about 10,000.

3. The composition of claim 1, comprising Formula V:

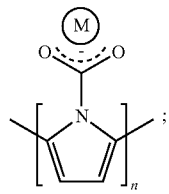

Formula V wherein M is a metal cation comprising a metal selected from the group consisting of Be, Mg, V, Cr, Mn, Fe, Co, Ni, Cu, Zn, Ga, As, Se, Rb, Ag, Cd, Cs, Ba, Au, Tl, Th, Pb, and U, or a rare earth element selected from the group consisting of La, Ce, Pr, Nd, Sm, Eu, Gd, Dy, Ho, Er, Tm, Yb, and Lu.

4. The composition of claim 1, wherein the composition is dispersed in an aqueous solution.

5. A method for removing a metal from a solution, the method comprising:
contacting a solution containing at least one metal with the composition of claim 1 in order to coordinate the metal to Formula A and thereby form a complex; and
removing the complex from the solution so as to remove the metal from the solution.

6. The method of claim 5, wherein the metal comprises Be, Mg, V, Cr, Mn, Fe, Co, Ni, Cu, Zn, Ga, As, Se, Rb, Ag, Cd, Cs, Ba, Au, Tl, Th, Pb, U, or a rare earth element comprising La, Ce, Pr, Nd, Sm, Eu, Gd, Dy, Ho, Er, Tm, Yb, or Lu, or a combination thereof.

7. The method of claim 5, wherein the solution comprises water from a natural water source or drinking water.

8. The method of claim 5, wherein the removing comprises passing the solution through a filter to remove the complex from the solution.

9. The method of claim 8, wherein the filter comprises pores having a size of about 0.2 microns.

10. A method for detecting or quantifying a metal, the method comprising:
dispersing the composition of claim 1 comprising a polymer into a solution containing a metal at a first concentration in order to chelate coordinate the metal to the polymer Formula A;
desorbing the metal from Formula A the polymer in order to produce a pre-concentrated solution containing the metal at a second concentration, wherein the second concentration is greater than the first concentration; and
analyzing the pre-concentrated solution to detect or quantify the metal.

11. The method of claim 10, wherein the dispersing of the composition comprises ultra-sonification.

12. The method of claim 10, wherein the desorbing is conducted with an acid.

13. The method of claim 10, wherein the metal comprises Be, Mg, V, Cr, Mn, Fe, Co, Ni, Cu, Zn, Ga, As, Se, Rb, Ag, Cd, Cs, Ba, Au, Tl, Th, Pb, U, or a rare earth element comprising La, Ce, Pr, Nd, Sm, Eu, Gd, Dy, Ho, Er, Tm, Yb, or Lu, or a combination thereof.

14. A composition comprising Formula IV:

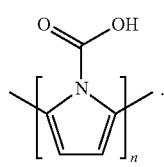

Formula IV wherein n is an integer greater than 1.

15. A composition comprising Formula A dispersed in a solution:

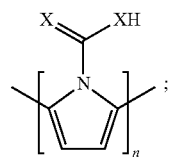

Formula A wherein:
  each X is independently either S or O, and
  n is an integer greater than 1;
or a salt, stereoisomer, racemate, hydrate, solvate, polymorph, or complex thereof;
wherein Formula A is uniformly dispersed in the solution.

16. The composition of claim 15, comprising Formula IV:

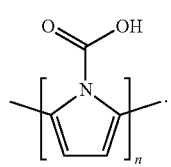

Formula IV

17. The composition of claim 15, comprising Formula II:

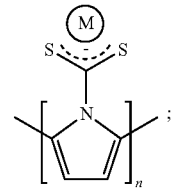

Formula II wherein M is a metal cation comprising a metal selected from the group consisting of Co, Ni, Cu, Zn, Cd, and Pb.

* * * * *

UNITED STATES PATENT AND TRADEMARK OFFICE
CERTIFICATE OF CORRECTION

PATENT NO. : 11,634,517 B2
APPLICATION NO. : 16/583751
DATED : April 25, 2023
INVENTOR(S) : Jon Kirchhoff, Ahmad Rohanifar and Govind Sharma Shyam Sunder It is certified that error appears in the above-identified patent and that said Letters Patent is hereby corrected as shown below:

In the Claims

Column 26, Claim 10, Line 47-51, please make changes from:
"dispersing the composition of claim 1 comprising a polymer into a solution containing a metal at a first concentration in order to chelate coordinate the metal to the polymer Formula A;
desorbing the metal from Formula A the polymer in order"

To:
--dispersing the composition of claim 1 into a solution containing a metal at a first concentration in order to coordinate the metal to Formula A;
desorbing the metal from Formula A in order--

Signed and Sealed this
Twentieth Day of June, 2023

Katherine Kelly Vidal
*Director of the United States Patent and Trademark Office*